United States Patent [19]
Biegajski et al.

[11] Patent Number: 5,700,478
[45] Date of Patent: Dec. 23, 1997

[54] WATER-SOLUBLE PRESSURE-SENSITIVE MUCOADHESIVE AND DEVICES PROVIDED THEREWITH FOR EMPLACEMENT IN A MUCOSA-LINED BODY CAVITY

[75] Inventors: James E. Biegajski, Foster City; Subbu S. Venkatraman, Palo Alto; Ann M. Scott, Mountain View, all of Calif.

[73] Assignee: Cygnus, Inc., Redwood City, Calif.

[21] Appl. No.: 505,185

[22] PCT Filed: Aug. 19, 1994

[86] PCT No.: PCT/US94/09305

§ 371 Date: Aug. 3, 1995

§ 102(e) Date: Aug. 3, 1995

[87] PCT Pub. No.: WO95/05416

PCT Pub. Date: Feb. 23, 1995

[51] Int. Cl.⁶ .............. A61F 6/06; A61F 9/02; A61K 9/70; A61K 47/30
[52] U.S. Cl. .............. 424/434; 424/430; 424/435; 424/436; 424/437; 424/443; 514/772.3; 514/777; 514/778; 514/780; 514/781; 514/782
[58] Field of Search ............. 424/430, 434, 424/435, 436, 437, 443; 514/772.3, 777, 778, 786, 781, 782

[56] References Cited

U.S. PATENT DOCUMENTS

| | | |
|---|---|---|
| Re. 33,093 | 10/1989 | Schiraldi et al. |
| 3,598,123 | 8/1971 | Zaffaroni |
| 3,998,215 | 12/1976 | Anderson et al. |
| 4,139,627 | 2/1979 | Lane et al. |
| 4,292,299 | 9/1981 | Suzuki et al. |
| 4,294,820 | 10/1981 | Keith et al. |
| 4,325,855 | 4/1982 | Dickman |
| 4,373,036 | 2/1983 | Chang et al. |
| 4,438,258 | 3/1984 | Graham |
| 4,460,562 | 7/1984 | Keith et al. |
| 4,503,070 | 3/1985 | Eby, III |
| 4,515,162 | 5/1985 | Yamamoto et al. |
| 4,517,173 | 5/1985 | Kiazawa |
| 4,529,748 | 7/1985 | Wienecke |
| 4,593,053 | 6/1986 | Jevne et al. |
| 4,713,243 | 12/1987 | Schiraldi et al. |
| 4,722,761 | 2/1988 | Cartmell et al. |
| 4,860,754 | 8/1989 | Sharik |
| 4,910,247 | 3/1990 | Haldar et al. |

(List continued on next page.)

FOREIGN PATENT DOCUMENTS

| | | |
|---|---|---|
| 681997 | 3/1964 | Canada |
| 63-171565 | 7/1988 | Japan |
| 63-174660 | 7/1988 | Japan |
| 2-59513 | 2/1990 | Japan |
| 2115431 | 9/1983 | United Kingdom |
| 91/16041 | 10/1991 | WIPO |

*Primary Examiner*—Carlos A. Azpuru
*Attorney, Agent, or Firm*—Morrison & Foerster LLP

[57] ABSTRACT

Water-soluble pressure-sensitive adhesives include a water-soluble polymer that is made tacky at room temperature by addition of a water-soluble plasticizer that is miscible with the polymer. Suitable polymers are solid at room temperature; and have a hydrophilicity as measured by water uptake greater than about 25%; they are liquid at room temperature and have a boiling point higher than about 80° C. The adhesives according to the invention may conveniently be provided in dry film form. Preferred water-soluble pressure-sensitive adhesives of the invention adhere both to mucosal surfaces and to a variety of materials that may constitute a part of a device or prosthesis to be held in a body cavity that has a mucosal lining. Also, a laminated device for the controlled release of a substance within a mucosa-lined body cavity includes the substance dissolved or dispersed in either or both of a water-soluble pressure-sensitive adhesive layer and optionally one or more water-soluble polymer layers. Also, devices for administering a substance over an extended time for relief of sore throat or cough, or for administering a breath freshening agent, particularly a mint odorant, include a water soluble polymer film layer containing the active ingredient, and a water soluble pressure sensitive mucoadhesive layer.

45 Claims, 12 Drawing Sheets

U.S. PATENT DOCUMENTS

| | | |
|---|---|---|
| 4,915,950 | 4/1990 | Miranda et al. . |
| 4,927,634 | 5/1990 | Sorrentino et al. . |
| 4,948,580 | 8/1990 | Browning . |
| 4,978,531 | 12/1990 | Yamazaki . |
| 5,024,701 | 6/1991 | Desmarais . |
| 5,047,244 | 9/1991 | Sanvordeker . |
| 5,064,717 | 11/1991 | Suzuki . |
| 5,158,825 | 10/1992 | Altwirth . |
| 5,166,233 | 11/1992 | Kuroya et al. . |
| 5,186,938 | 2/1993 | Sablotsky et al. . |
| 5,271,940 | 12/1993 | Cleary et al. . |
| 5,455,043 | 10/1995 | Fischel-Ghodsian . |

1

WATER-SOLUBLE PRESSURE-SENSITIVE MUCOADHESIVE AND DEVICES PROVIDED THEREWITH FOR EMPLACEMENT IN A MUCOSA-LINED BODY CAVITY

This application is a 371 of PCT/US94/09305 filed Aug. 19, 1994.

BACKGROUND

1. Technical Field

This invention relates to mucoadhesives and to mucoadhering devices. Additionally and particularly this invention relates to compositions that adhere both to mucosal surfaces and to a variety of materials that may constitute a part of a device or prosthesis to be held in a body cavity, such as the oral cavity or the vagina or the rectum, that has a mucosal lining. Additionally this invention relates to mucoadhering devices useful for controlled release of substances within a body cavity that has a mucosal lining, such as for example the oral cavity, and particularly to such devices that are provided with adhesives suitable for fixation of the device within the oral cavity. Additionally and particularly this invention relates to administering breath-freshening agents, and particularly mint odorants, into the oral cavity of a person over extended time periods, for freshening the person's breath. And additionally this invention relates to administering agents into a person's oral cavity over extended times for relief of sore throat pain and cough.

2. Background Art

For a number of practical purposes, it can be useful to affix a device within a mucosa-lined body cavity, such as the oral cavity, the vaginal cavity, or the rectal cavity. Devices that may usefully be positioned within a mucous-lined body cavity include, for example, denture prostheses and devices for controlled release of medicaments.

In one approach for such purposes, the device can be affixed to a mucosal surface of the body cavity by means of an adhesive. Various bioadhesives have been proposed for use in establishing adhesive contact with mucosal surfaces.

For example, U.S. Pat. No. 4,713,243 describes an extruded film for use in controlled release of medicaments, including a water-soluble or swellable polymer matrix capable of adhering to a wet mucous surface, made up of 40–95% hydroxy propyl cellulose, 5–60% poly(ethylene oxide), optionally up to 10% of a water-insoluble polymer (ethyl cellulose, propyl cellulose, polyethylene or polypropylene) and 2–10% of a plasticizer introduced to facilitate processing, and containing the medicament. There is no disclosure in the '243 patent that this composition can adhere to materials that may be used in oral prosthesis or other devices, or that it is pressure-sensitive.

Adhesives for affixing dental prostheses in the mouth are conventionally in the form of pastes or creams. These are messy and inconvenient to use, and generally adhere poorly or not at all after extended periods.

U.S. Pat. No. 4,529,748 describes a dental prosthesis adhesive in powder form, in which the particles are made from carboxy methyl cellulose, poly(ethylene oxide), poly (acrylic acid), and karaya gum. Some portion of the particles are coated with a cellulose or acrylate polymer film that dissolves slowly in saliva.

U.S. Pat. No. 4,948,580 describes a bioadhesive composition for delivery of anti-bacterials, including a copolymer of ("PVME/MA"), and gelatin, dispersed in an ointment base.

International Patent Publication No. WO 91 16041 (Oct. 31, 1991) describes a pharmaceutical composition, to be held under the tongue, in the form of a thin starch wafer capable of molding to the contours of the sub-lingual cavity, thereby allowing for absorption of medicaments contained within the wafer through the sub-lingual mucosa.

Conventionally, medications for treatment for relief of sore throat and cough are provided in a form such as a lozenge to be held in the mouth of the person being treated, or in the form of a mouthwash or spray. These forms of delivery work generally by shedding the medication into the saliva, which bathes the tissues of the oral cavity and throat as it passes posteriorly toward the esophagus. Such forms remain in the oral cavity only for short periods of time, generally in the range up to about 10 or 20 minutes, and they cannot provide for delivery of the medication to the oral cavity over extended times. In these forms the treatment must be readministered at short time intervals to be effective. The rate at which the medication is delivered from a lozenge can depend upon how actively the user agitates it, that is, how vigorously the user sucks on the lozenge, and whether the user breaks it with the teeth.

Moreover, the presence of a lozenge in the user's mouth can be annoying or distracting, and may interfere with speech or with ingestion of fluids. Holding the lozenge in the mouth—that is, avoiding either swallowing it or spitting it out—requires conscious effort, and inadvertent loss can be embarrassing.

U.S. Pat. No. 4,927,634 (May 22, 1990) describes a incorporation of Dyclonine HCl and phenol into base vehicles such as lozenges, drops or troches. U.S. Pat. No. 4,503,070 (Mar. 5, 1985) describes administering zinc gluconate to the oral mucosa in the form of a troche or lozenge to reduce the duration of common cold symptoms.

U.S. Pat. No. 4,139,627 (Feb. 13, 1979) describes including a pharmaceutically acceptable acid in a process for making a lozenge containing Dyclonine HCl; the acid acts as a stabilizing agent during processing to prevent degradation of the Dyclonine HCl.

Nearly everyone at least occasionally has malodorous breath. Bad breath may be caused by consumption of strongly flavored food or drink or by use of tobacco, for example, or it may be caused by poor oral hygiene. It may be a symptom of, or may result from, a disease or metabolic condition. The condition may be temporary or chronic, and may be mild, so as to be merely somewhat unpleasant, or may be so severe as to interfere with ordinary social interaction.

Because bad breath (often termed "halitosis", particularly when the condition is severe) is so common a source of embarrassment, considerable attention has been directed to trying to prevent or mask it. In some instances, the condition may not be prevented except by correction of an underlying disease or metabolic disorder, or by improvement in oral hygiene. Some instances of halitosis are so extreme that they cannot be masked. Many cases of ordinary bad breath can be masked by use of an odorant in the mouth and throat that contributes a pleasant smell to the exhalant breath of the person. In many cultures, various mint odorants are commonly accepted on the breath.

Odorants, such as mint odorants, are conventionally administered to the mouth in the form of a spray or mouthwash. Sprays and mouthwashes provide only very temporary mask, as they are quickly washed away by ordinary salivary secretions.

Also conventionally, odorants are administered in a lozenge, or in chewing gum. Lozenges can provide for somewhat more extended administration than sprays or mouthwashes, as the odorant is continuously shed as the lozenge dissolves in the saliva. Chewing gums can also provide for somewhat more extended administration, although the odorant may after some fairly short time be delivered at such a slow rate as not to be effective. As note above, the presence of a lozenge or chewing gum in the person's mouth can be annoying or distracting, and may interfere with speech or with ingestion of fluids. Other persons can be distracted or annoyed by a person's chewing gum, and in some social circumstances chewing gum is not accepted.

SUMMARY OF THE INVENTION

We have discovered water-soluble pressure-sensitive mucoadhesives that can be used for affixing devices within a mucosa-lined body cavity. The water-soluble pressure-sensitive adhesives of the invention can be used in construction of devices for emplacement within a body cavity that has a mucosal lining, as for example on a mucosal surface within the body cavity. Some of the water-soluble pressure-sensitive mucoadhesives according to the invention additionally adhere to a variety of materials, such as polymers, that are conventionally employed in the construction of devices, such as dental prostheses, which are held in the mouth.

Thus the mucoadhesive compositions according to the invention can be used to affix any device within the body cavity, such as, for example, a dental plate. For placement within the oral cavity, for example, the adhesive preferably is made from materials generally regarded as safe ("GRAS-certified"), or national formulary ("NF-certified"), and therefore safe for oral use or for ingestion.

The pressure-sensitive adhesives of the invention are fully water-soluble, and are thus fully soluble in secretions present in mucous-lined body cavities. Consequently, the adhesive eventually dissolves completely within the body cavity in which it is placed, and the dissolved or dispersed matter is flushed away with the fluid secretions of the cavity or, in the case of use in the oral cavity, passes on to the alimentary canal. Pressure-sensitive adhesives according to the invention require no moistening prior to contact with the mucosal or the polymer surface.

The adhesives are additionally particularly useful in construction of laminated devices for controlled delivery of substances within a mucosa-lined body cavity. The invention therefore provides devices having an adhesive surface suitable for affixing to a mucous surface of a mucosa-lined body cavity such as the mouth or throat, the vagina, or the rectum, or that is suitable for affixing to the dental surface or to the surface of various forms of prosthesis that may be used in the body cavity, such as for example dentures. Devices according to the invention are provided in various configurations, each configuration providing for controlled delivery of one or more substances from a single device according to one of a variety of schedules. Selected devices according to the invention can provide, for example, delayed onset delivery, pulsed delivery, and sequential delivery of two or more substances.

In some configurations, the adhesive itself serves as a reservoir for the substance to be delivered, and releases the substance into the body cavity as the adhesive dissolves. In some configurations a laminate construction includes at least one polymer layer in addition to the adhesive layer. Each such configuration releases one or more substances according to a desired timed delivery regime. In various configurations, for example, onset of release may be delayed following placement of the device within the body cavity; or, for example, a substance may be released at different rates over time, or in pulses with intervening periods in which substantially no release occurs; or, for example, two or more substances may be sequentially released, with or without an intervening period in which substantially no substance is released. The pattern of release is established according to the invention by the sequential arrangement of laminae containing the substance(s) and, in some configurations, laminae not containing the substance(s) or containing fewer than all the substances. The release rate for a substance from a particular layer is determined principally by the rate at which the layer dissolves or disperses in the fluid milieu of the body cavity, together with the concentration of the substance in the layer. Release from a particular more basally situated layer is delayed by overlying layer(s), and the duration of the delay in delivery from such a particular layer is determined principally by the time required for the overlying layer(s) to disperse.

To a limited extent, whether or not a particular layer dissolves or disperses in the fluid milieu of the body cavity, a substance may in time move diffusionally out from the layer, so that the concentration of the substance within the layer fails. Such diffusional movement may result in release of the substance into the body cavity or, where the layer is the mucoadhesive layer, release of the substance transmucosally through the contacting mucosal surface. Or, where the particular layer is covered by an overlying layer, the substance may diffuse into and through the overlying layer. Where such diffusional release is undesirable, it may be limited by rendering the overlying layer substantially impermeable to the substance, so that release from the overlain layer is occluded until such time as the overlying layer has dissolved or dispersed. Suitably occluding layers can be constructed of a water-soluble polymer composition containing as an additive a nonorganic filler such as silica gel, or a fatty acid filler such as magnesium stearate, or a wax such as a paraffin, for example. For extended delayed onset, for example, a slow-dissolving substantially substance-impermeable top layer can be constructed of a hydrophobic material such as hydroxypropyl cellulose, thereby achieving a temporary occlusive (partially occlusive, at least effect. Such a modification may be made by a change in the polymer constituents of the top layer, or by introduction of additives into the layer itself.

The adhesive can be mucoadhesive, or it can adhere to the surface of the teeth or to a variety of materials, such as polymers, that can be used in the construction of devices that are emplaced within the mucosa-lined body cavity (such as, for example, poly(methyl methacrylate), commonly used in dental prosthesis in the oral cavity). Some adhesives according to the invention are mucoadhesive and adehere to polymer surfaces such as PMMA. The adhesive can be a moistenable adhesive or, alternatively and in some instances preferably, it can be a pressure-sensitive adhesive.

In some embodiments of laminated devices of the invention all the layers are water-soluble (or, for example, are digestible), and they therefore dissolve or disperse entirely in the fluids secreted within the body cavity. In such embodiments the adhesive layer and the additional polymer layer(s) dissolve and are carried away at or following the time when the substance(s) have diffused away from the device. Preferred materials for the polymer layers as well as for the adhesive layers are for some applications therefore GRAS-certified or NF-certified, so that they are fully acceptable for oral use and for ingestion by humans.

We have further discovered that active substances, useful for relief of sore throat or of cough, can be delivered into the oral cavity over extended times by including the active substance within a water soluble pressure sensitive mucoadhesive device, and applying the mucoadhesive device to a mucosal surface within the oral cavity.

Such a device for temporary relief of sore throat or cough may be a layered composite, including a polymer layer that contains the active substance, and a mucoadhesive layer that serves to affix the active-containing layer to a mucosal surface such as the palate, the gum, or the cheek. Because the materials of the layers are water soluble, and therefore fully soluble in secretions present in mucous-lined body cavities, the device eventually dissolves completely within the oral cavity, and passes on to the alimentary canal. As the material of the active-containing layer dissolves in the fluid secretions, within the oral cavity, the active disperses in the fluid secretions and is distributed throughout the oral cavity and on to the throat.

In many applications delivery of an active substance into a mucosa-lined body cavity desirably is provided over an extended time. We have developed polymer compositions that dissolve slowly within the fluid secretions of the oral cavity, and that can include an active substance and can be deployed in a suitably thin layer within the oral cavity to deliver the active substance over extended times in excess of 1 hour. A desired rate of dissolution for a particular device configuration can be selected by choice of materials and proportions of materials in the active-containing polymer composition. Generally, the dissolution rate, together with the thickness of the active-containing polymer layer, determines the extent of the delivery time for the active substance.

The rate of delivery of the active substance over the delivery time can be selected by choosing an appropriate amount of the active substance in the active-containing layer as well as by choosing an appropriate polymer composition. Polymer compositions according to the invention are capable of delivery of active substances over extended times.

Preferred water soluble adhesives may be permeable to particular active substances; that is, while the active substance is released into the oral cavity as the active-containing polymer layer dissolves, it may additionally pass by diffusion into and through the adhesive layer, and then into and through the mucosal surface onto which the adhesive layer is affixed. Where delivery of the active substance to the mucosa underlying the device is not desired, an additional water-soluble layer, poorly permeable to the active substance, may be interposed between the active-containing layer and the adhesive layer, to substantially prevent movement of the active substance into the adhesive layer.

Any of a variety of active substances may be delivered using delivery devices constructed according to the invention. For relief of sore throat pain, for example, substances such as benzocaine, lidocaine, dyclonine, and the like, which are available over the counter in syrup or tablet form, may be used. For relief of cough, for example, substances such as dextromethorphan HBr, noscpine, codeine phosphate, menthol, and the like, may be used. Further, both a sore throat medication and a cough suppressant can be combined within and delivered from a single device according to the invention.

The invention provides for continuous delivery of the medication over an extended time, providing for relief of sore throat pain for longer times, in the range up to about 1 to 4 hours, than can be provided by conventional means. Location of the disc on the upper palate helps localize the medication nearer to the site of soreness upon swallowing during normal salivary flow.

We have further discovered that odorants suitable for masking bad breath, and particularly mint odorants, can be administered into the oral cavity over extended times by including the odorant within a suitable water soluble pressure sensitive mucoadhesive device, and applying the mucoadhesive device to a mucosal surface within the oral cavity.

The breath freshening device may be a layered composite, including a water soluble polymer layer that contains the mint odorant, and a water soluble mucoadhesive layer that serves to affix the odorant-containing layer to a mucosal surface such as the palate, the gum, or the cheek. Because the materials of the layers are water soluble, and therefore fully soluble in secretions present in mucous-lined body cavities, the device eventually dissolves completely within the oral cavity, and the dissolved material passes on to the alimentary canal. As the material of the odorant-containing layer dissolves in the fluid secretions, within the oral cavity, the odorant disperses in the fluid secretions and is distributed throughout the oral cavity.

We have developed polymer compositions that dissolve slowly within the fluid secretions of the oral cavity, and that can include an odorant and can be deployed in a suitably thin layer within the oral cavity to deliver the odorant over extended times in excess of 1 hour. A desired rate of dissolution for a particular device configuration can be selected by choice of materials and proportions of materials in the odorant-containing polymer composition. Generally, the dissolution rate, together with the thickness of the odorant-containing polymer layer, determines the extent of the delivery time for the odorant.

The rate of delivery of the odorant over the delivery time can be selected by choosing an appropriate amount of the odorant in the odorant-containing layer. Polymer compositions according to the invention are capable of delivering odorants over extended times at high enough concentrations to contribute a continuous pleasant smell to the exhalant breath sufficient to mask bad breath odor.

Preferred water soluble adhesives may be permeable to certain mint odorant components; that is, certain of the mint odorant components may by diffusion pass into and through the adhesive layer, to the mucosal surface onto which the adhesive layer is affixed. Because some mint odorant components may be irritating to the mucosa or may cause an unpleasant local numbing effect on the mucosa when present in higher amounts, it may be desirable to avoid delivery of the odorant to the underlying mucosa. This can be accomplished according to the invention by interposing an additional water-soluble layer, poorly permeable to the odorant components, between the odorant-containing layer and the adhesive layer, to substantially prevent movement of the odorant components into the adhesive layer.

Any of a variety of odorants may be delivered according to the invention, and any of various mint odorants, as described below, may be particularly desirable.

Because the device according to the invention remains affixed to a surface of the oral cavity during use, no conscious effort by the user is required to hold the device in place, and the likelihood that it may be swallowed or spit out of the mouth during use is diminished. As the device has a thin profile, and conforms smoothly to the surface of the oral cavity, it is not mechanically annoying and does not interfere with speech or with ingestion of foods or fluids.

DISCLOSURE OF THE INVENTION

Water-Soluble Pressure-Sensitive Adhesives

In one general aspect, the invention features a water-soluble pressure-sensitive adhesive including a water-soluble polymer that is made tacky (that is, it is rendered pressure-sensitive) at room temperature by addition of a water-soluble plasticizer that is miscible with the polymer. Suitable polymers are characterized as being solid at room temperature (that is, as having a glass transition temperature T(g), or melting point T(m), higher than about 25° C., and more preferably higher than about 30° C., and lower than about 120° C., and more preferably lower than about 100° C.); and having a hydrophilicity as measured by water uptake greater than about 25%. Suitable plasticizers are characterized as being liquid at room temperature and having a boiling point higher than about 80° C.

Suitable polymers include polysaccharides such as for example cellulose-type materials and natural gums, polypeptides, and water-soluble synthetic polymers. Particular examples of such suitable polymers which are GRAS certified include poly(vinyl pyrrolidone) ("PVP"), poly (vinyl alcohol) ("PVA"), hydroxy propyl cellulose ("HPC"), poly(ethylene oxide) ("PEO"), poly(acrylic acid) ("PAA"), polyacrylates such as Carbopol 934 (B. F. Goodrich), starch and starch derivatives, polysaccharides, sodium carboxymethyl cellulose ("Na-CMC"), xanthan gum, karaya gum, and gelatin, among others. Suitable plasticizers include, for example and particularly for oral-mucosal contact and other use in the oral cavity, glycerin, sorbitol, any of the glycols, polysorbate 80, triethyl titrate, acetyl triethyl titrate, and tributyl titrate.

In some embodiments for oral mucosal contact and for skin contact, a water-soluble pressure-sensitive adhesive according to the invention includes PVP (about 95–40 weight %) and, optionally, HPC (up to about 50 weight %) as a polymer; and glycerin as a plasticizer (about 5–35 weight %). Optionally, any balance (up to about 30 weight %) can be made up by water. By way of illustration, such compositions adhere instantaneously (within less than five seconds) to oral mucosal surfaces and to oral cavity prostheses or other devices of the poly(methyl methacrylate) ("PMMA") type, as well as to human skin.

In other embodiments for oral mucosal contact and for skin contact, a water-soluble pressure-sensitive adhesive according to the invention includes as a polymer HPC (about 0–50 weight %) and, optionally, (up to about 50 weight %) one or more of PVP, PVA, PEO, starch, polysucrose or other polysaccharide, xanthan gum, or karaya gum; and glycerin as a plasticizer (about 11–60 weight % and, preferably about 30–50 weight % for PVP- or HPC-containing adhesive compositions). In these formulations, the HPC preferably has a molecular weight between about 60 k and about 1,000 k, and more preferably between about 100 k and about 300 k.

In another general aspect, the invention features a water-soluble pressure-sensitive adhesive film made up of a water-soluble polymer that is made tacky (that is, it is rendered pressure-sensitive) at room temperature by addition of a water-soluble plasticizer that is miscible with the polymer.

In preferred embodiments the thickness of the film is in the range of about 5–20 mils, and is shaped to fit and to conform generally to a mucosal surface-contacting portion of a dental prosthesis such as a dental plate. Preferred water-soluble pressure-sensitive adhesive films according to the invention are very flexible, and are therefore capable of conforming to and adhering to contoured surfaces such as the gum or the roof of the mouth. Such a film can be used as a denture adhesive, that can adhere to oral mucosal surfaces and to dental prosthesis for an extended period, typically of more than about 5 hours. The film can be used as part of a system for delivery of substances through the oral mucosa (as a buccal transmucosal patch), or for delivery of substances into the oral cavity itself.

Device Having a Water-Soluble Pressure-Sensitive Adhesive for Emplacement in a Mucosa-Lined Body Cavity In another general aspect, the invention features a laminated device for controlled release of one or more substances within a mucosa-lined body cavity, having an adhesive layer by means of which the device can be affixed within the body cavity.

In some embodiments the mucoadhesive layer is water-soluble, constructed in some embodiments of a water-soluble moistenable mucoadhesive, and in some embodiments of a water-soluble pressure-sensitive mucoadhesive; in some embodiments the adhesive adheres to a variety of materials, such as polymers, that can be used in construction of devices for emplacement on a mucosal surface or within a body cavity that has a mucosal lining; or it is mucoadhesive and additionally adheres to such materials. Preferably the water-soluble pressure-sensitive adhesive requires no moistening prior to contact with the mucosal or the polymer surface. For placement within the oral cavity, for example, the adhesive preferably is made from materials generally regarded as safe ("GRAS-certified"), or national formulary ("NF-certified"), and therefore safe for oral use or for ingestion.

Preferred water-soluble pressure-sensitive adhesives for use in the adhesive layer of the invention are those according to the invention, as disclosed above under the heading "Water-Soluble Pressure-Sensitive Adhesives", and as described in further detail hereafter. Accordingly they include a water-soluble polymer that is rendered tacky (that is, it is rendered pressure-sensitive) at room temperature by addition of a water-soluble plasticizer that is miscible with the polymer.

In some embodiments for oral mucosal contact, a water-soluble pressure-sensitive adhesive according to the invention includes PVP (about 95–65 weight %) and, optionally, HPC (up to about 50 weight %) as a polymer; and glycerin as a plasticizer (about 5–35 weight %). Optionally, any balance (up to about 30 weight %) can be made up by water. By way of illustration, such compositions adhere well to oral mucosal surfaces and to oral cavity prostheses or other devices of the poly(methyl methacrylate) ("PMMA") type.

In other embodiments for oral mucosal contact a water-soluble pressure-sensitive adhesive according to the invention includes as a polymer HPC (about 100–50 weight %) and, optionally, (up to about 50 weight %) one or more of PVP, PVA, PEO, starch, polysucrose or other polysaccharide, xanthan gum, or karaya gum; and glycerin as a plasticizer (about 5–35 weight %). In these formulations, the HPC preferably has a molecular weight between about 60 k and about 1,000 k, and more preferably between about 100 k and about 300 k. The water-soluble pressure-sensitive adhesive layer may take the form of a film which preferably is about 5–10 mils thick. Preferred water-soluble pressure-sensitive adhesive films according to the invention are very flexible, and are therefore capable of conforming to and adhering to contoured surfaces such as the gum or the roof of the mouth.

In preferred embodiments the device includes at least one water-soluble polymer layer in addition to the water-soluble pressure-sensitive adhesive layer. This water soluble polymer layer is a hydrophobic material that will not dissolve in cold water (below about 40° C.) and has little or no tendency to hydrate with water. The material may further be hot water dispersible and may have non-tacky surface properties upon moistening. Examples of suitable GRAS-certified materials include but are not limited to monoglycerides, triglycerides, waxes such as paraffin, fatty acids, fatty alcohols and mixtures thereof. In a particular embodiment, sorbitan monostearate (SPAN 60) with hydroxypropyl cellulose (HPC LF) is useful.

The pressure-sensitive adhesive layer and, in some embodiments, one or more of the polymer layers in the device according to the invention are fully water-soluble, and are thus fully soluble in secretions present in mucous-lined body cavities. Consequently, the pressure-sensitive adhesive layer and the water-soluble polymer layers eventually dissolve completely within the body cavity in which the device is placed, and the material of the dissolved layers is flushed away with the fluid secretions of the cavity or, in the case of use in the oral cavity, passes on to the alimentary canal.

According to the invention, the adhesive serves to keep the device in place within the body cavity, and release of the substance or substances is controlled by the particular arrangement of layers.

Device for Controlled Release of Substance within a Mucosa-Lined Body Cavity In a further general aspect, the invention features a device for emplacement within a mucosa-lined body cavity of a subject, the device including a portion made of a water-soluble pressure sensitive adhesive composition. A surface of the water-soluble pressure sensitive adhesive portion forms a basal surface of the device which, when the device is in use, is affixed to a surface of the body cavity.

The adhesive compositions providing an adhesive surface of the device of the invention are pressure-sensitive; that is, the adhesive surface of the device requires no wetting prior to contacting it with the body cavity surface to which it is to be affixed.

The adhesive compositions are fully water-soluble, and are thus fully soluble in secretions present in mucous-lined body cavities. Consequently, the adhesive eventually dissolves completely within the body cavity in which the device is placed, and is flushed away with the fluid secretions of the cavity or, in the case of use in the oral cavity, passes on to the alimentary canal. For placement within the oral cavity, for example, the adhesive preferably is made from materials generally regarded as safe ("GRAS-certified"), or national formulary ("NF-certified"), and therefore safe for oral use or for ingestion.

Preferred water-soluble pressure-sensitive adhesives for use in the adhesive layer of the invention are those according to the invention, as disclosed above under the heading "Water-Soluble Pressure-Sensitive Adhesives", and as described in further detail hereafter. Accordingly they include a water-soluble polymer that is rendered tacky (that is, it is rendered pressure-sensitive) at room temperature by addition of a water-soluble plasticizer that is miscible with the polymer.

In some embodiments the device is emplaced within the body cavity by contacting the adhesive surface with a mucosal surface within the body cavity or with a surface of a prosthesis that is employed within the body cavity, and for such embodiments the water-soluble pressure sensitive adhesive composition preferably includes PVP (about 95–40 weight %) and, optionally, HPC (up to about 50 weight %) as a polymer; and glycerin as a plasticizer (about 5–35 weight %). Optionally, any balance (up to about 30 weight %) can be made up by water. By way of illustration, such compositions adhere instantaneously (within less than five seconds) to mucosal surfaces as well as to surfaces of prostheses or other devices of the poly(methyl methacrylate) ("PMMA") type.

In other embodiments, a water-soluble pressure-sensitive adhesive according to the invention includes as a polymer HPC (about 0–50 weight %) and, optionally, (up to about 50 weight %) one or more of PVP, PVA, PEO, starch, polysucrose or other polysaccharide, xanthan gum, or karaya gum; and glycerin as a plasticizer (about 11–60 weight % and, preferably about 30–50 weight % for PVP- or HPC-containing adhesive compositions). In these formulations, the HPC preferably has a molecular weight between about 60 k and about 1,000 k, and more preferably between about 100 k and about 300 k. In some embodiments the device is a device for delivery of one or more substances into the body cavity or across the mucosa. Typically the device has a laminated structure, and the water-soluble pressure sensitive portion is a basal layer of the device. Conveniently, the water-soluble pressure sensitive adhesive portion of such a device is constructed as a film made up of an adhesive composition as described above. In preferred embodiments the film has a thickness in the range about 5–20 mils, and is shaped to fit and to conform generally to the surface to which the device is intended to be attached for use. Preferred water-soluble pressure-sensitive adhesive films according to the invention are very flexible, and are therefore capable of conforming to and adhering to contoured surfaces such as the gum or the roof of the mouth.

In some embodiments the device when in place within the body cavity provides a protective barrier for the area of the mucosal surface to which it is affixed which is covered by the device. The barrier may protect the underlying mucosal surface from mechanical abrasion or erosion, for example, or, for example, it may serve to protectively isolate the underlying mucosal surface from some substance in the fluid of the milieu of the body cavity.

Where the device is a laminated device for delivery of an active agent, and includes an upper active-containing layer laminated to an adhesive layer, or where the device provides a protective barrier, and includes an upper barrier layer laminated to an adhesive layer, the upper layer is preferably constructed of a hydrophobic polymer material that will not dissolve in cold water (below about 40° C.) and has little or no tendency to hydrate with water. The material may further be hot water dispersible and may have non-tacky surface properties upon moistening. Examples of suitable GRAS-certified materials include but are not limited to monoglycerides, triglycerides, waxes such as paraffin, fatty acids, fatty alcohols and mixtures thereof.

The rate of release of the active substance within the oral cavity depends to at least some extent upon the rate of dissolution or dispersion of the polymer of the active layer in situ, which in turn varies substantially according to the molecular weight of the principal polymer component: a given polymer type dissolves or disperses more slowly at higher molecular weights than at lower molecular weights.

In some embodiments the active-containing layer includes a polymer such as hydroxypropyl cellulose, and may additionally include a plasticizer such as glycerin. In a particular embodiment, hydroxypropyl cellulose (HPC Klucel LF), having a molecular weight of 80,000, with glycerin as a plasticizer, is useful.

Long-Lasting Mucoadhesive Device for Temporary Relief of Sore Throat and Cough

In yet another general aspect, the invention features a layered composite mucoadhesive device for delivery of an active substance into the oral cavity, having an active-containing layer that includes the active substance dispersed or dissolved in a water soluble polymer, and a water soluble adhesive layer.

In some embodiments the active-containing water soluble polymer layer is a hydrophobic material that will not dissolve in cold water (below about 40° C.) and has little or no tendency to hydrate with water. The material may further be hot water dispersible and may have non-tacky surface properties upon moistening. As noted above examples of suitable GRAS-certified materials include but are not limited to monoglycerides, triglycerides, waxes such as paraffin, fatty acids, fatty alcohols and mixtures thereof.

Also as noted above, the rate of release of the active substance within the oral cavity depends to at least some extent upon the rate of dissolution or dispersion of the polymer of the active layer in situ, which in turn varies substantially according to the molecular weight of the principal polymer component; a desired release rate can be specified by choice of the polymer or polymer combination.

In some embodiments the adhesive for use in the adhesive layer of the invention is a water-soluble pressure-sensitive adhesive according to the invention, as disclosed above under the heading "Water-Soluble Pressure-Sensitive Adhesives", and as described in further detail hereafter. Accordingly such adhesives include a water-soluble polymer that is rendered tacky (that is, it is rendered pressure-sensitive) at room temperature by addition of a water-soluble plasticizer that is miscible with the polymer.

Additional ingredients, such as, for example, deodorants or reodorants or flavorants, may be delivered along with the active substance as the active-containing layer disperses within the oral cavity. Such additional ingredients include, for example, sweeteners such as aspartame, and breath fresheners such as menthol.

In another general aspect the invention features a method for administering a substance over an extended time period for relief of sore throat or cough. The method involves dissolving or dispersing the substance in a laminated water soluble device that has a water soluble pressure sensitive adhesive layer. The device is affixed to the mucosal surface of the oral cavity.

Long-Lasting Mucoadhesive Device for Administration of Breath-Freshening Agent

In still another general aspect, the invention features a laminated composite device for administering an odorant into the oral cavity over an extended time. The device has at least two layers, including a basal layer constructed of a water soluble pressure sensitive mucoadhesive polymer composition; and an odorant-containing water soluble polymer layer.

In some embodiments the basal adhesive layer is mucoadhesive and additionally adheres to a variety of materials, such as polymers, that can be used in construction of devices for emplacement on an oral mucosal surface or within the oral cavity. The basal adhesive layer preferably is constructed of a water soluble pressure sensitive adhesive that requires no moistening prior to contact with the mucosal or the polymer surface. The adhesive preferably is made from materials generally regarded as safe ("GRAS-certified"), or national formulary ("NF-certified"), and therefore safe for oral use or for ingestion.

Preferred water-soluble pressure-sensitive adhesives for use in the adhesive layer of the invention are those disclosed above under the heading "Water-Soluble Pressure-Sensitive Adhesives", and described in further detail hereafter. Accordingly such adhesives include a water-soluble polymer that is rendered tacky (that is, it is rendered pressure-sensitive) at room temperature by addition of a water-soluble plasticizer that is miscible with the polymer.

In some embodiments the odorant containing layer includes a polymer such as a hydroxypropyl cellulose, and in a particular embodiment may additionally include a plasticizer such as glycerin. The rate of release of the odorant within the oral cavity can be specified by selection of particular polymer or polymer combinations, as noted generally above under the heading "Device for Controlled Release of Substance within a Mucosa-Lined Body Cavity". In a particular embodiment, a hydroxypropyl cellulose (HPC Klucel GF), having a molecular weight of 300,000, is useful.

The water soluble odorant containing layer may take the form of a film which preferably is about 20–30 mils thick. Suitable slow-dissolving polymers such as HPC are typically not sufficiently flexible to conform with the irregularly curved surfaces of the oral cavity or of oral or dental prostheses, and addition of a plasticizer to the polymer or polymer mixture of films would be required for these applications. Suitable plasticizers can include glycerin, for example.

In some embodiments the odorant is an essential oil of a plant material, or a refined fraction of an essential oil, or a combination of the chief aromatic constituents of an essential oil. Preferably the odorant is a mint odorant. We have discovered that, surprisingly, the essential oils that are commonly used as flavorings, particularly oil of wintergreen, oil of peppermint, and oil of spearmint, are themselves effective as plasticizers. For breath freshener devices for delivering a mint odorant, therefore, the odorant containing layer therefore can consist of the polymer and the mint odorant (and, optionally, a sweetener and a preservative), without any requirement for a plasticizer other than the mint odorant.

Accordingly, in another aspect the invention features a laminated composite device for administering a mint odorant into the oral cavity over an extended time, comprising a basal layer constructed of a water soluble pressure sensitive mucoadhesive composition and an upper layer containing a water soluble polymer, such as a HPC, and a mint oil.

Extended delivery of odorant can be obtained according to the invention from devices whose composite thickness is 35 mils or less. The devices according to the invention are very flexible, and are therefore capable of conforming to and adhering to contoured surfaces such as the gum or the roof of the mouth. Breath freshening devices according to the invention can deliver a mint odorant such as a peppermint continuously over a period of up to two hours or longer from a single device, and can provide breath freshening for even greater periods of time.

DESCRIPTION OF PREFERRED EMBODIMENTS

Preferred embodiments of the invention will now be described, beginning with a brief description of the drawings.

Figure 1:
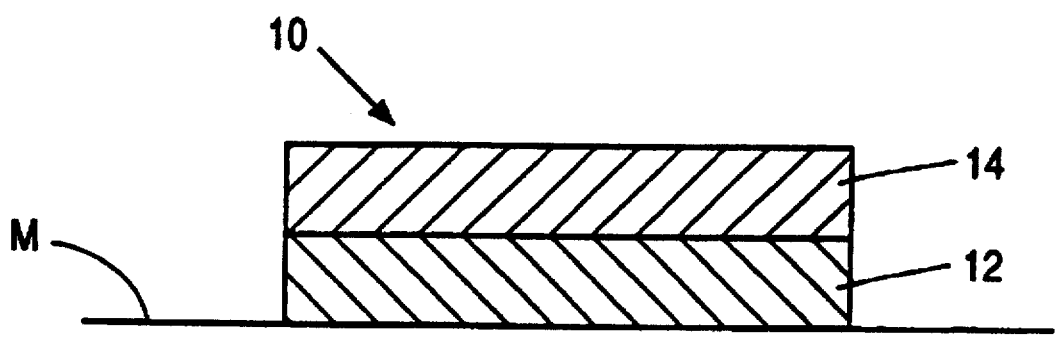
FIG. 1 is a sketch in sectional view showing a device of the invention configured to provide delivery of One or more substances at two different rates.

As will be appreciated, the drawings are not made to scale, and, in particular, no attempt has been made to represent relative thicknesses of the layers proportionately, and the thicknesses of the various layers are exaggerated for clarity of presentation.

MODES OF CARRYING OUT THE INVENTION

Water-Soluble Pressure-Sensitive Adhesives

1. Preparation of a water-soluble pressure-sensitive adhesive composition made up of PVP and glycerin.

A solution of poly(vinyl pyrrolidone) ("PVP": Kollidon®, obtained from BASF) and glycerin was first prepared in isopropyl alcohol ("IPA"), in the following proportion by weight: 15 parts PVP, 6 parts glycerin, and 79 parts IPA. The solution was coated on a polyester release liner and allowed to dry at room temperature for 15 hours to permit evaporation of the IPA. The resulting dry film is both pressure-sensitive and water-soluble.

Measurements of tack were made using a TA.XT2 Texture Analyzer (Texture Technologies Corp.) together with an XT.RA Dimension software package (Stable Micro Systems, Ltd.), as follows. A sample of the film on a release liner is mounted upon a block, and a probe is moved at a fixed speed against the adhesive surface of the film, distorting the film to a fixed penetration depth, where the probe is permitted to dwell for a fixed time. The probe is then withdrawn from the film, at a fixed speed, and the peak force required to detach the probe from the film surface is measured as a measure of tack.

Measured tack of samples of a PVP-glycerin film prepared as described above and having 5 mils thickness was 1820 g/cm$^2$, using a probe diameter of 0.80 cm, a penetration depth of 0.1 mm, a penetration rate of 1.0 mm/sec, a dwell time of 10 sec, and a withdrawal rate of 5.0 mm/sec. Typical tack values for adhesives used in transdermal devices, for example, are about 1000-2000 g/cm$^2$.

Measurements of water solubility were made by submersion of a sample of the film in water at 21° C., stirring the water, and determining the time required for apparent complete dissolution of the film.

The total measured dissolution time of samples of a PVP-glycerin film prepared as described above and having 5 mils thickness was about 10 minutes.

2. Preparation of a water-soluble pressure-sensitive adhesive composition made up of HPC, PVP and glycerin.

Hydroxy propyl cellulose ("HPC"), PVP and glycerin were first blended in the proportion, by weight, of 4 parts HPC, 2 parts PVP, and 2 parts glycerin. The resulting mixture was pressed in a heated Carver laboratory press at 200° F. to a thickness about 35 mils. The resulting film was flexible, translucent and tacky at room temperature.

3. Preparation of dental prosthesis adhesive film.

A water-soluble pressure-sensitive adhesive film made as described above can be die-cut in a shape that conforms to that portion of the dental prosthesis that closely fits the mucosal surface of the mouth, such as the part of the dental plate that fits against the palate. The shaped film pieces can be packaged dry. For use, the dry film is pressed onto the appropriate surface of the dental prosthesis so that it adheres. Then the dental prosthesis with the adhesive affixed is inserted into the correct position in the mouth and pressed against the mucosal surface until adhesion is achieved.

The following Example is intended to illustrate but not to limit the invention.

EXAMPLE I

Breath Freshening Device

A dissolvable mucoadhesive device capable of releasing a flavor into the oral cavity was constructed as follows: A solution was made up by co-dissolving 15.4 grams of polyvinyl pyrrolidone PVP (K90) and 6.0 grams of glycerin in 80 grams of isopropanol (IPA). The resulting solution was coated at a thickness of 30 mils onto a polyester release liner and allowed to dry for 15 hours at room temperature. The resulting dry film was tacky at room temperature and had a final thickness of about 5 mils. A second solution containing 43 grams of IPA, 42 grams of water, 15 grams of HPC EF, 2.5 grams of peppermint oil and 3.0 grams of Nutrasweet™ brand sweetener containing aspartame was prepared by mixing all the components until fully dissolved. The solution was then coated at a thickness of 50 mils onto a polyester release liner. The film was allowed to dry at room temperature for 15 hours to a final thickness of about 5 mils.

The two dry films were laminated together. Discs having a diameter of about 1.2 cm were cut from the laminate. The discs were tested in vivo by adhering a single disc to the upper palate of three volunteers. The discs adhered well to the mucosal surface and upon hydration with saliva immediately began releasing peppermint oil and aspartame as noticed by taste. The total time of dissolution in the mouth was about 10 minutes, during which time a pleasant, refreshing mint flavor was perceived.

Device Having a Water-Soluble Pressure-Sensitive Adhesive for Emplacement in a Mucosa-Lined Body Cavity 1. Water-soluble pressure-sensitive adhesive layer.

The preferred water-soluble pressure-sensitive adhesive layer of the device according to the invention provides the foundation upon which the device operates. There follows first a description, by way of examples, of protocols for making exemplary water-soluble pressure-sensitive adhesives and films suitable for use in the adhesive layer.

a. Preparation of a water-soluble pressure-sensitive adhesive composition made up of PVP and glycerin.

A solution of poly(vinyl pyrrolidone) ("PVP": Kollidon®, obtained from BASF) and glycerin was first prepared in isopropyl alcohol ("IPA"), in the following proportion by weight: 15 parts PVP, 6 parts glycerin, and 79 parts IPA. The solution was coated on a polyester release liner and allowed to dry at room temperature for 15 hours to permit evaporation of the IPA. The resulting dry film is both pressure-sensitive and water-soluble.

Measurements of tack were made using a TA.XT2 Texture Analyzer (Texture Technologies Corp.) together with an XT.RA Dimension software package (Stable Micro Systems, Ltd.), as follows. A sample of the film is first mounted onto a block, and a probe is moved at a fixed speed against the adhesive surface of the film, distorting the film to a fixed penetration depth, where the probe is permitted to dwell for a fixed time. The probe is then withdrawn from the film, at a fixed speed, and the peak force required to detach the probe from the film surface is measured as a measure of tack.

Measured tack of samples of a PVP-glycerin film prepared as described above and having 5 mils thickness was 1820 g/cm$^2$, using a probe diameter of 0.80 cm, a penetration depth of 0.1 mm, a penetration rate of 1.0 mm/sec, a dwell time of 10 sec, and a withdrawal rate of 5.0 mm/sec. Typical tack values for adhesives used in transdermal devices, for example, are about 1000–2000 g/cm$^2$.

Measurements of water solubility were made by immersing a sample in water at 21° C., stirring the water, and determining the time required for apparent complete dissolution of the film.

The total measured dissolution time of samples of a PVP-glycerin film prepared as described above and having 5 mils thickness was about 10 minutes.

b. Preparation of a water-soluble pressure-sensitive adhesive composition made up of HPC, PVP and glycerin.

Hydroxy propyl cellulose ("HPC"), PVP and glycerin were first blended in the proportion, by weight, of 4 parts HPC, 2 parts PVP, and 2 parts glycerin. The resulting mixture was pressed in a heated Carver laboratory press at 200° F. to a thickness about 35 mils. The resulting film was flexible, translucent and tacky at room temperature.

2. Device configurations.

a. Device having two substance-containing layers:

Referring to FIG. 1, there is shown by way of example a device 10 having a basal adhesive layer 12 which in use adheres to mucosal surface M and an upper polymer layer 14, in which a substance or substances to be delivered are contained in both layers. As the upper layer is bathed by the fluids in the body cavity (for example by saliva and ingested fluids in the mouth), dissolution of the upper layer begins first and is substantially complete when dissolution of the basal layer begins. Where a different substance is contained in each layer, the substances are released sequentially. The two layers can be made to have different dissolution rates or swelling rates, resulting in one release rate for the substance or substances in the basal adhesive layer, and another release rate for the substance or substances in the upper polymer layer. If, for instance, the dissolution rate of the upper layer is slower than that of the lower layer, the resulting release regime is of a slow release of the substance in the upper layer, followed by a relatively rapid release of the substance in the basal layer. Or, alternatively, the two layers can have approximately the same dissolution rates, but be loaded with the substance at different concentrations, resulting in a higher rate of delivery from that layer having the substance present in higher concentration.

Figure 5:
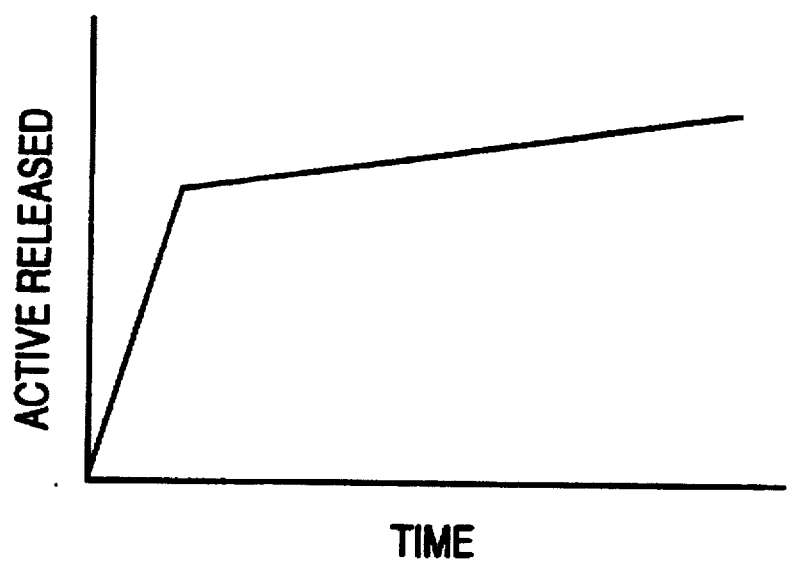
FIGS. 5 through 7 are rough hypothetical plots showing quantity of an active substance released by devices of the invention configured on the plans shown in FIGS. 1 through 3, respectively.

FIG. 5 shows a rough diagrammatic plot of the release of active over time from a device made on the plan in FIG. 1. As will be appreciated, the different rates need not be linear, nor need the break between the rates be abrupt as shown.

Such a configuration can be useful in a breath freshener for oral use, by way of example, in which the basal layer can have a relatively slow dissolution rate and can be loaded with an antimicrobial, while the upper layer can have a relatively fast dissolution rate and can be loaded with a flavor or a reodorant. Such can result in a rapid release of flavorant or reedorant after emplacement in the mouth, followed by a slower release of the antimicrobial. Or, both layers can be loaded with a microbial, resulting release in an early burst followed by a more sustained delivery.

In one embodiment of this configuration, the basal layer is made of a polymer that becomes sticky on moistening, such as, e.g., HPC or PAA.

Figure 2:
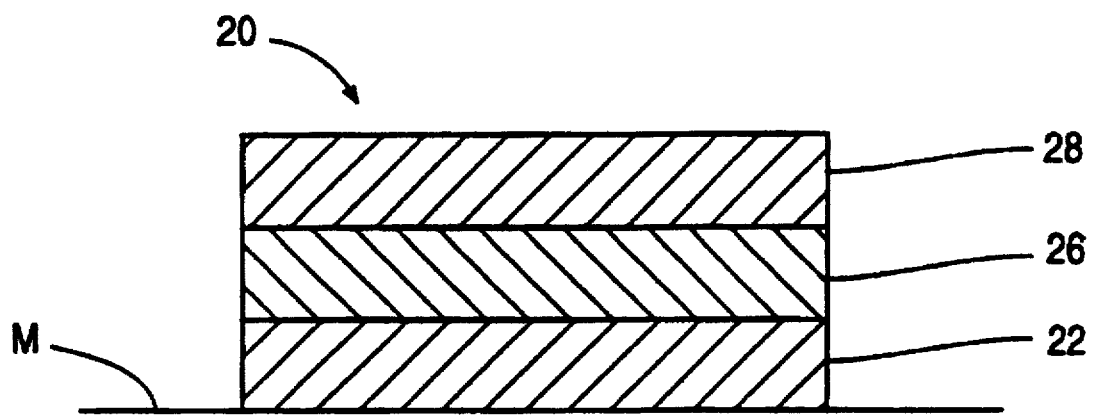
FIG. 2 is a sketch in sectional view showing a device of the invention configured to provide delayed-onset delivery of one or more substances.

In a modification of this configuration, the two layers described above can constitute middle and upper layers, respectively, of a three-layer device that is provided with a basal layer that is a water-soluble pressure-sensitive adhesive, so that the device need not be moistened prior to placement within the body cavity. As is described above, suitable compositions for such an adhesive layer include PVP as a polymer (95–65 weight %) and glycerine as plasticizer (5–35 weight %).

b. Device providing delayed-onset delivery:

Referring now to FIG. 2, there is shown a device 20 having a basal adhesive layer 22 which in use adheres to the mucosal surface M, a middle substance-containing water-soluble layer 26, and an upper layer 28, not containing the substance, that dissolves relatively slowly in the fluid environment of the body cavity. As in the device shown in FIG. 1, the adhesive layer is a water-soluble adhesive, which may be a mucoadhesive that becomes tacky when moistened. More preferably, the basal adhesive layer is a water-soluble pressure-sensitive adhesive as described above; and in some embodiments the middle layer is eliminated and the substance to be delivered in loaded into the adhesive layer. However, where loading is so high (upwards of 25% by weight, for example) that it would compromise the adhesive capacity of the adhesive layer, a system having the substance to be delivered loaded in a middle layer can be preferred.

Figure 6:
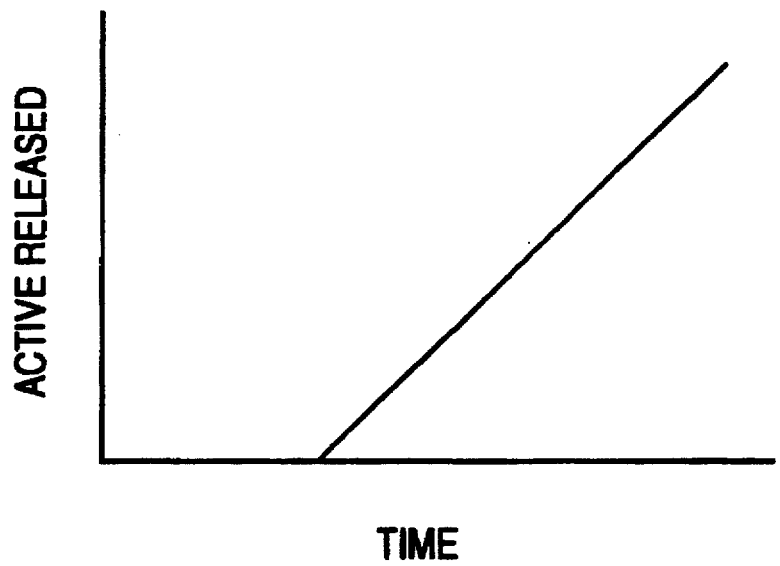

FIG. 6 shows a rough plot of the amount of active released over time from a device made on the plan of FIG. 2. Here, as in FIG. 5, the rate need not be linear, nor need the onset be abrupt as shown.

Figure 3:
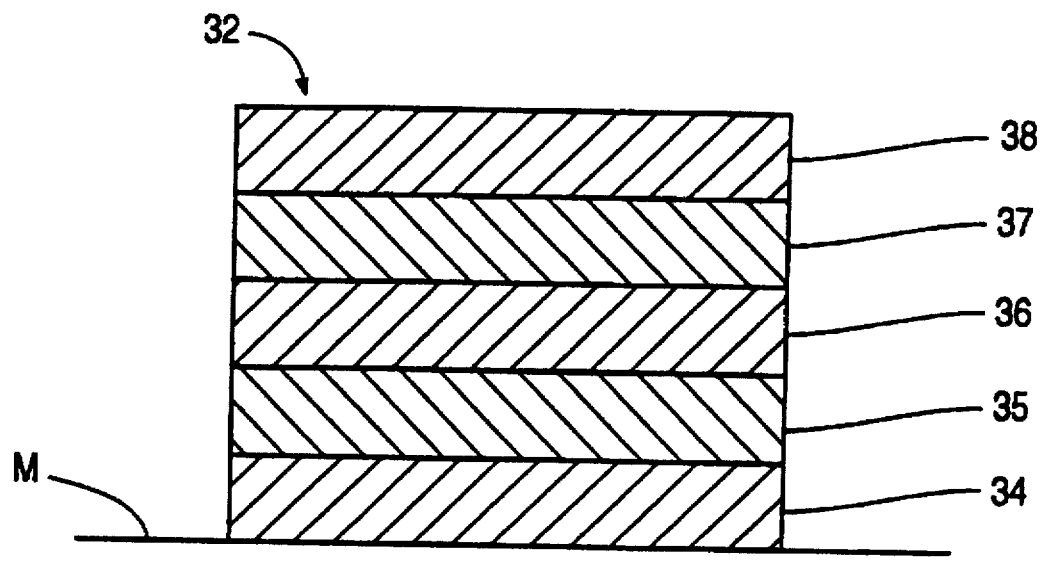
FIG. 3 is a sketch in sectional view showing a device of the invention configured to provide delivery of one or more substances in a sequence of pulses.

Such a delayed-onset release configuration can be useful, by way of example, in a breath freshener that can be emplaced in the mouth before retiring for sleep, and which provides for release several hours later, so that the breath is fresh upon waking.

c. Device providing pulsed delivery:

A more complex release pattern can be achieved using several layers, in which alternating layers contain the active, as shown by way of example in FIG. 3. The basal adhesive layer 34 of device 32 can be made, as in the devices of FIGS. 1 and 2, either as a moistenable adhesive, or as a water-soluble pressure-sensitive adhesive. A moistenable adhesive may be preferred for reasons of greater stability. Basal layer 34 adheres to mucosal surface M when the device is in use and contains a substance to be delivered. Layers 36, 38 contain a substance to be delivered, while alternating layers 35, 37 are slowly dissolving layers not containing the substance.

Figure 7:
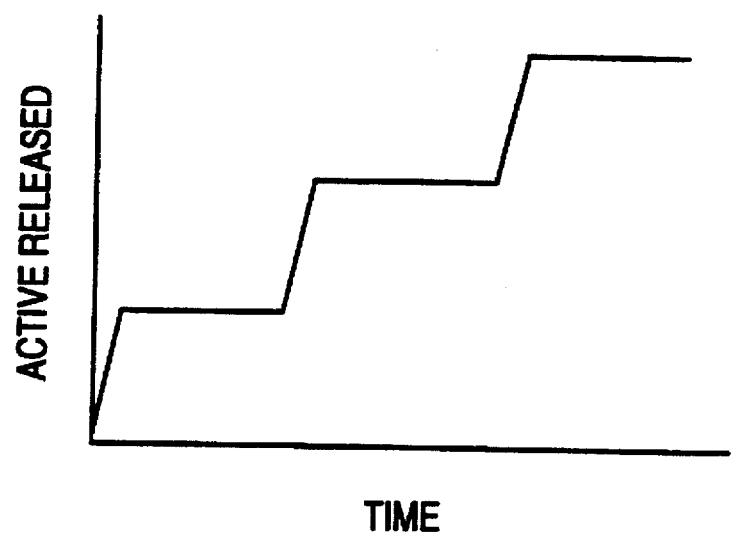

FIG. 7 shows a rough plot of the amount of active released over time from a device made on the plan of FIG. 3. Here, as in FIGS. 5 and 6, the rates for each delivery phase need not be linear, nor need the onset be abrupt as shown.

Such a configuration can be useful, for example, in an oral after-meals breath freshener, which provides for release of a flavor or reodorant or deodorant at intervals corresponding with post-mealtimes, with no release during mealtimes or at other times.

Such a configuration can be useful, to cite another example, for pulsed delivery of actives that can be toxic if administered continuously. Such actives include, by way of example, anti-bacterials such as Cetyl Pyridinium Chloride ("CPC"); pulsed release can give adequate antibacterial protection without raising toxicity concerns.

d. Device having suppressed marginal release.

Figure 4:
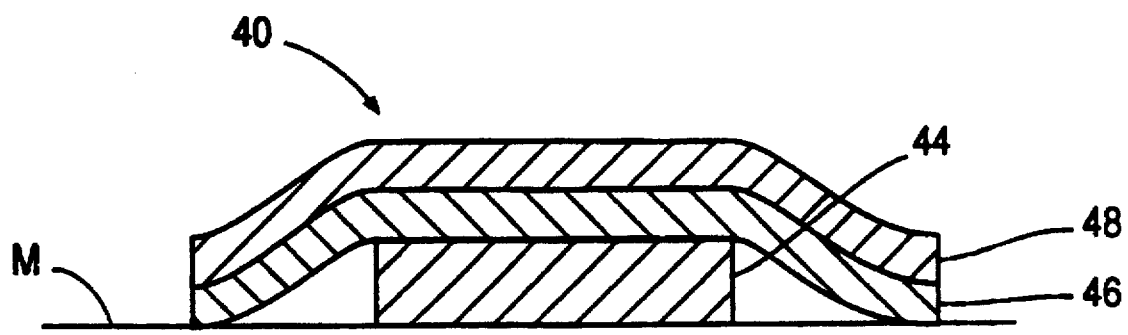
FIG. 4 is a sketch in sectional view showing a device of the invention configured to provide delayed-onset delivery of one or more substances while minimizing diffusion of the substance(s) at the edges of the device.

In any of the devices described above, dissolution at the edges or margins of the device, as well as from the upper surface, can be expected to result in release of the substance or substances within the layers whose edges are exposed. Loss of the desired release pattern can result, particularly where, as in FIG. 2, delayed onset is desired, or where, as in FIG. 3, pulsed release is desired. To minimize loss from the margins, a peripheral adhesive can be provided, as shown in FIG. 4, by way of example of a delayed onset release device having a marginal adhesive. The device 40 includes a moistenable mucoadhesive layer 44 containing the substance or substances to be delivered, which in use adheres to the mucosal surface M, and which is overlain by a water-soluble pressure-sensitive adhesive layer 46 whose edges extend beyond the edges of the mucoadhesive layer 44 on all sides and there adhere to the mucosal surface, forming a seal to prevent escape of the substance from the edges of the mucoadhesive layer 44 until the water-soluble pressure-sensitive adhesive layer has dissolved. The water-soluble pressure-sensitive adhesive layer is in turn covered by a slowly dissolving layer 48 not containing the substance. The slowly dissolving layer 48 provides a delay before the water-soluble pressure-sensitive adhesive begins to dissolve, which in turn prevents release of the substance until the upper surface of the substance-containing mucoadhesive layer is exposed.

Examples of substances that can be delivered within the oral cavity include: reodorants such as peppermint oil and other flavors, deodorants such as for example the odor-preventive antimicrobial CPC, anti-bacterials such as chlorhexidine, sore-throat medicants such as Hexylresorcinol/Phenol derivatives/Menthol, cough suppressants such as Dextrathomorphan Hydochloride, agents to prevent mouth dryness, benzocaine for treatment of rhinitis, etc.

3. Particular devices.

EXAMPLE II

Two-Layer Device Having a Water-Soluble Pressure-Sensitive Adhesive Layer

A two-layer device according to the invention was made according to the following protocol. First the necessary components (polymers, additives, etc.) for each layer were dissolved or dispersed in an appropriate solvent. For an upper layer, the casting solution in one prototype consisted of 41 parts isopropyl alcohol ("IPA"), 40 parts water, 14 parts hydroxypropyl cellulose ("HPC") EF (MW~80,000), 2.4 parts peppermint oil and 2.8 parts Aspartame. The casting solution for the basal layer consisted of 79 parts IPA, 15 parts poly(vinyl pyrrolidone) ("PVP") (Kollidon 90), and 6 parts glycerin. Each of these two casting solutions was coated onto a polyester release liner, to provide a substratum for forming the layer, at the desired thicknesses of 50 mils for the upper layer and 25 mils for the basal layer. The layers were then allowed to dry on the respective release liners overnight (at least 15 hours) at room temperature inside a hood). The dry films were then carefully hand-laminated together to provide a two-layer system consisting of a non-tacky upper layer containing the substances to be released, and an adjacent tacky pressure-sensitive-adhesive soluble basal layer.

Alternatively, manufacture of the pressure sensitive adhesive device can be carried out by extruding a blend of the components for each layer through a slit die to form a thin film. The upper and basal films can then be laminated together through rollers, with the tacky layer protected by a release liner from contact with the rollers.

Alternately, the substances to be delivered (e.g., peppermint oil or other printable material or materials) can be printed onto an extruded pure HPC EF or other similar extruded film, as described in Miranda et al. U.S. Pat. No. 4,915,950, which is hereby incorporated by reference.

EXAMPLE III

Two-layer Device Having a Moistenable Mucoadhesive Layer, and Capable of Delivering at Two Different Constant Rates An alternative two-layer device according to the invention was made as follows. The upper layer was made by first co-dissolving HPC HF and CPC in IPA in the following proportions: 10 parts HPC EF, 0.135 parts CPC, and 90 parts IPA. The solution was then coated at a thickness of 15 mils onto a polyester release liner, and allowed to dry at room temperature overnight (at least 15 hours). This film formed an upper layer having a dry thickness of 1.5 mils. The basal layer was made by first co-dissolving HPC EF, CPC and IPA in the following proportions: 2 parts HPC HF, 0.0054 parts CPC, and 98 parts IPA. The solution was then coated at a thickness of 50 mils onto a polyester release liner, and dried in an oven at 70° C. for 6 hours. The dry film was then collected and ground to a coarse powder using a mortar and pestle. This powder was then pressed in a heated Carver laboratory press to form a film having a thickness about 2 mils. Then the upper (LEF) and basal (HF) films were laminated together and then bonded by compressing in a heated (275° F.) Carver press.

EXAMPLE IV

Multilayer Device Providing Pulsed Release

A multilayer device was made by first co-dissolving poly(vinyl propylene) ("PVP") (K 90), glycerine, methylene blue and IPA in the following proportions: 7.2 parts PVP (90), 2.8 parts glycerine, 90 parts IPA and 0.030 parts methylene blue. The solution was coated onto a polyester release liner at a thickness about 25 mils wet, and then dried at room temperature for 15 hours. The resulting dry film constituted the active layer material. A second film was prepared by pressing HPC EF powder to a thickness of about 4 mils, using the heated Carver press.

The PVP/glycerin/methylene blue film and the HPC EF film were then arranged in alternating fashion to produce a laminate of six layers, three containing and three not containing the substance to be delivered. The PVP/glycerin/methylene blue layers served as an adhesive to bond the laminate composite, and served as a reservoir for the substance (methylene blue, in this illustrative example) to be released from each layer as it dissolved. The HPC EF layers provided for periods of time between releases, providing the pulsed release profile.

EXAMPLE V

Delayed-Onset Device

A delayed-onset device was made by first blending hydroxypropyl cellulose (HPC LF) and sorbitan monostearate (SPAN 60) as dry powders in a 1:1 ratio by weight. This blend was pressed using a heated Carver press at 200° F. to a thickness of 15 mils. The resulting polymer film was flexible having a waxy, hydrophobic surface.

An adhesive film was made by blending the following components:

| HPC MF | 1.0 gram |
| Kollidon PVP (K90) | 2.0 grams |
| Glycerin | 2.0 grams |

After blending at room temperature, the resulting mixture was pressed in a heated Carver press at 200° F. to a thickness of 10 mils. This adhesive layer was used to adhere the HPC LF:SPAN 60 film to the top layer of the 25 min. breath disc described above in Example II.

The multilayer disc was tested over-night by adhering the disc to the upper palate just prior to going to sleep for the night. There was no noticeable mint flavor initially and during the several minutes thereafter before actually falling asleep. Approximately 5.5 hours later, however, the disc released a burst of peppermint oil into the mouth strong enough to stimulate and awaken the wearer.

Device for Controlled Release of Substance within a Mucosa-Lined Body Cavity Any of a variety of devices, in any configuration and for any intended use when emplaced within a body cavity of a subject, are within the scope of the claims. The invention is illustrated below by way of example only; the examples are not intended as limiting the scope of applicants' contribution to the art, and other types and arrangements of devices are within the scope of the invention.

EXAMPLE VI

Laminated Composite Device for Delivery of Antimicrobial

Figure 12:
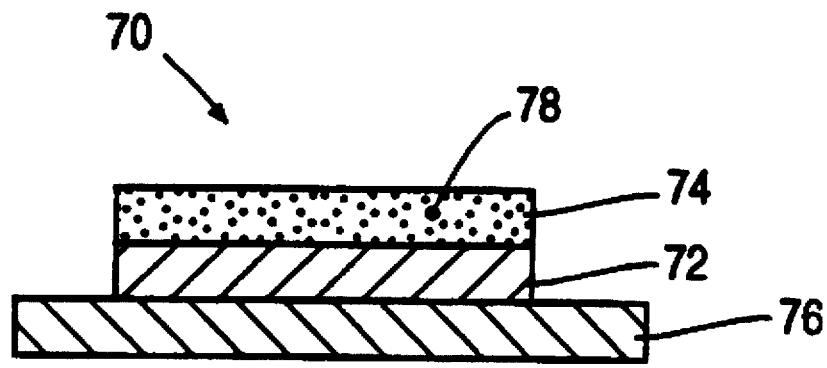
FIG. 12 is a sketch in sectional view showing another embodiment of a device according to the invention.

By way of example of a device according to the invention that can be affixed to a mucosal surface of a body cavity to provide delivery of an active substance into the body cavity, FIG. 12 shows generally at 70 a device having a basal water-soluble pressure-sensitive adhesive layer 72, and an overlying polymer layer 74 containing the active substance 78. The device is shown removably affixed by the adhesive surface to a release liner 76.

The adhesive layer can be constructed as follows. An HPC polymer is thoroughly mixed with a poly vinylpyrrolidone ("PVP") polymer, with glycerol as a plasticizer, with a food colorant, and with a preservative (BHA), and the resulting mixture is formed and pressed to a thickness of 5 mils. For this particular example, the components were mixed in the following proportions.

| PVP (K90) | 47.0% |
| Glycerin | 37.0 |
| Klucel HPC GF | 16.0 |
| FD & C #40 | 0.024 |
| BHA | 0.0020 |

This resulting adhesive film was then laminated to the active containing film, described below, to form a bilaminate composite 30 mils thick. Disks having diameter ½ inch were then die cut from the bilaminate composite.

Disks formed as described above, ½ inch in diameter and 30 mils thick have an active substance-containing layer weighing approximately 100 milligrams.

The active containing layer can be constructed as follows. Using 85 grams of ethyl alcohol as the solvent, 13.5 grams of hydrohypropyl cellulose (HPC EF) was dissolved with stirring with 1.5 g CPC. The mixture was blended until uniform, at which time the thickened solution was cast as a film onto a release liner and left in a hood overnight to allow the solvent to evaporate, forming a dried film. The dried film was pressed using a heated Carver press to form an active containing layer of 25 mils thickness.

The tack and work of adhesion of the adhesive surface of the device as described in this example, as an indication of its adhesive properties, was measured for three samples as follows.

Sample 1 peak: −0.561 kg; area: −0.0177 kg
Sample 2 peak: −0.420 kg; area: −0.0097 kg
Sample 3 peak: −1.306 kg; area: −0.0352 kg

EXAMPLE VII

Protective Barrier Device

Figure 13:
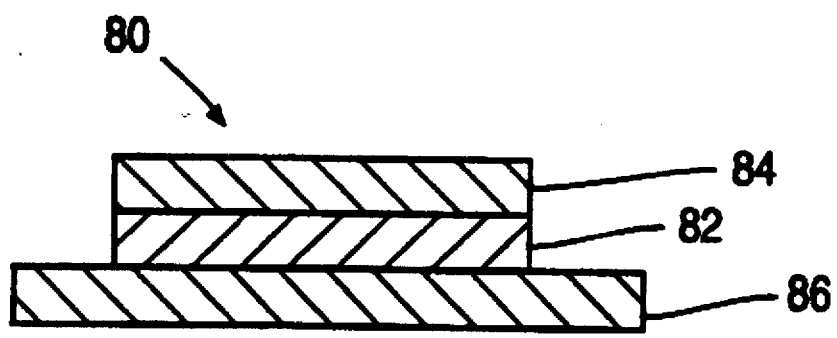
FIG. 13 is a sketch in sectional view showing another embodiment of a device according to the invention.

Additionally by way of example of a device according to the invention that can be affixed to a mucosal surface of a body cavity to provide a protective barrier for the underlying mucosal surface, FIG. 13 shows generally at 80 a device having a basal water-soluble pressure-sensitive adhesive layer 82, and an overlying protective layer 84 constructed of a relatively abrasion-resistant water soluble polymer. The device is shown removably affixed by the adhesive surface to a release liner 86.

In this example, the adhesive layer can have the composition, and can be constructed, as described generally above and particularly, for example, as described for the adhesive layer of Example VI.

The overlying protective layer can be constructed, for example, of a water soluble polymer as would be suitable for an active containing layer for delivery into the body cavity; and the protective layer can be constructed as described generally and particularly above. Particularly suitable polymers include for example HPC HF, polyvinyl alcohol ("PVA"), and hydroxymethyl cellulose.

A device made according to this example can be used, for example, as a temporary covering for an area of injury to the mucosal surface, such as an area of cheek of lip that has been abraded or cut. Or, the device can provide an abrasion preventive for areas of mouth tissue that are subject to abrasion by, for example, orthodontural devices.

Long-Lasting Mucoadhesive Device for Temporary Relief of Sore Throat and Cough

1. Construction of the device

Preparation of a mucoadhesive disc for containing a sore throat medication.

A medication-containing mucoadhesive laminated disc according to the invention can be made by forming and then laminating an adhesive film and an active substance-containing polymer film generally as follows.

a. The adhesive layer. A water-soluble adhesive layer can be formed from an adhesive polymer film, according to the following general protocol. First, the polymer (or polymers) and the plasticizer are thoroughly mixed, using where necessary a suitable solvent such as ethyl alcohol. Where a solvent is used, the resulting mixture is then coated on a release liner, and the solvent is allowed to evaporate to produce a dry film. Dry film samples are then collected and pressed to the desired final film thickness. Where no solvent is used, the mixture can be pressed to a film of the desired thickness.

b. The active substance-containing layer. First, the polymers and one or more desired active agents and one or more desired flavorants are dissolved, for example by stirring, in an appropriate solvent. Then the resulting thickened solution is formed into a thin (wet) film, for example by casting onto a release liner, and then the solvent is permitted to evaporate to a dry film. Then the dry film is pressed to a desired thickness and is affixed, for example by pressing, onto an adhesive layer prepared as described above.

Hydroxypropyl cellulose (HPC) can be a particularly suitable polymer for construction of the active-containing layer. HPC dissolves completely in aqueous fluids such as the fluids of the oral cavity, and within a selected range of molecular weights, HPC dissolves (or disperses) in the oral cavity sufficiently slowly to provide substantially continuous delivery of the active substance over an extended period. HPC is flexible, so that it conforms well to irregular curved surfaces of the oral cavity; HPC is not tacky when moistened, and has a pleasant texture in the mouth. It is thus comfortable and unobtrusive for the user. HPC blends well with a variety of active substances.

Glycerol, which may be added as a plasticizer in the active-containing layer, may additionally (or alternatively) act to inhibit crystallization of some active substances that might otherwise occur at the loading concentrations employed (for example, menthol).

c. Laminated devices are then cut from the laminated film by, for example, die-cutting, to the desired size and shape. Typically, circular or oval shapes may be preferred. The devices can be stored on a release liner affixed to the adhesive surface, and removed from the liner as needed by the user.

Figure 8:
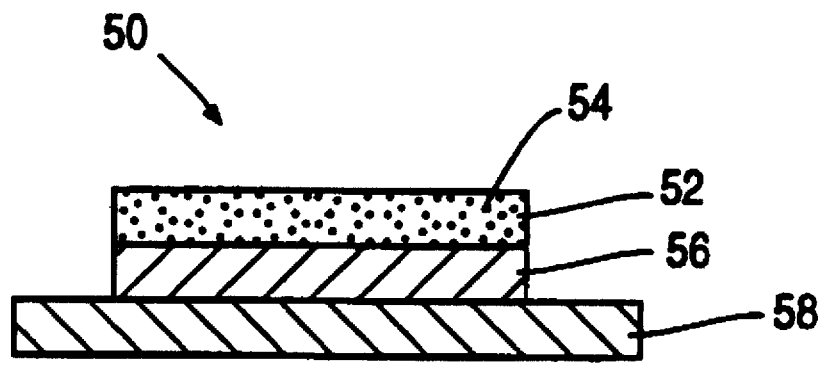
FIG. 8 is a sketch in transverse sectional view showing a bilaminate device according to the invention.

A laminated device according to the invention may be bilaminate, having an adhesive layer and an active-containing layer, as shown for example in transverse sectional view in FIG. 8. Or, the device may be trilaminate, having a third water soluble layer, poorly permeable to the active substance, interposed between the adhesive layer and the active-containing layer, as shown for example in transverse sectional view in FIG. 9. This layer may be made of a material such as for example polvinyl acetate ("PVAc") or ethyl cellulose, or such, for example, one of the Eudragit family of polymethacrylic copolymers commercially available from Rohm (e.g., Eudragit S100, L100, E100, L100-55). The Eudragit polymethacrylic copolymers are characterized by being variously soluble at various pH; Eudragit S100 has a suitably low solubility at the typical pH of the normal human saliva. The interposed third layer may where desired be made more flexible by addition of a plasticiser such as, for example, glycerine, in amount up to, for example, about 20%.

Referring now to FIG. 8, a bilaminate device 50 includes a polymer layer 52 containing the active substance 54, laminated onto an adhesive layer 56. The device is shown removably affixed to a release liner 58.

Figure 9:
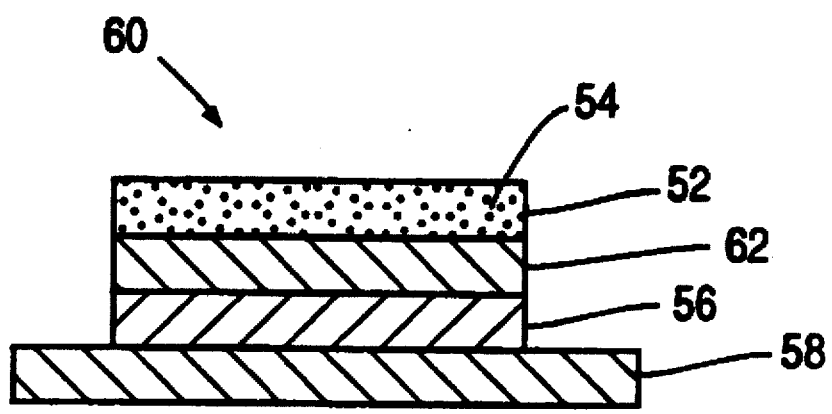
FIG. 9 is a sketch in transverse sectional view showing a trilaminate device according to the invention.

Referring to FIG. 9, a trilaminate device 60 includes a third polymer layer 72, poorly permeable to the active substance, laminated between polymer layer 62 containing the active substance 64, laminated onto an adhesive layer 66. The device is shown removably affixed to a release liner 68.

2. Use of the device

As the need for relief of sore throat or cough arises, the user simply peels a laminated device away from the release liner, and affixes it to a surface within the oral cavity. It can be preferred to affix the device to the mucosal surface at the roof of the mouth, as that provides for direct flow of the active substance toward the rear of the mouth and the throat.

The following examples, are intended for illustration only, and are not intended to limit the scope of the invention.

EXAMPLE VIII

Disc for Delivery of Cineole

The active containing layer was constructed as follows. Using 80 grams of ethyl alcohol as the solvent, the following materials were dissolved with stirring in order of appearance:

| | |
|---|---|
| Glycerin | 1.0 grams |
| Cineole | 1.0 grams |
| Aspartame | 0.3 grams |
| Menthol | 1.7 grams |
| HPC Klucel LF | 16 grams |

The mixture was blended until uniform, at which time the thickened solution was coated to a thickness of 50 mils wet onto a release liner and left in a hood overnight to allow the solvent to evaporate, forming a dried film. The dried film was pressed using a Carver press under 20,000 p.s.i. at 200° F. for 1–2 min., to form an active containing layer of 25 mils thickness.

The adhesive layer was constructed as follows. An HPC polymer was thoroughly mixed with a poly vinylpyrrolidone ("PVP") polymer, with glycerol as a plasticizer, with a food colorant, and with a preservative (BHA), and the resulting mixture was formed and pressed to a thickness of 5 mils. For this particular example, the components were mixed in the following proportions.

| | |
|---|---|
| PVP (K90) | 47.0% |
| Glycerin | 37.0 |
| Klucel HPC GF | 16.0 |
| FD & C #40 | 0.024 |
| BHA | 0.0020 |

This resulting adhesive film was then laminated to the active containing film, described above, to form a bilaminate composite 30 mils thick. Disks having diameter ½ inch were then die cut from the bilaminate composite.

Disks formed as described above, ½ inch in diameter and 30 mils thick have an active substance-containing layer weighing approximately 100 milligrams. Such a layer (and the disc) therefore contains 8.5 milligrams of menthol and 5 milligrams of cineole.

EXAMPLE IX

Disc for Delivery of Dyclonine HCl

The active containing layer was formed as follows. Using 80 grams of ethyl alcohol as the solvent, the following materials were dissolved with stirring in order of appearance:

| | |
|---|---|
| Glycerin | 2.0 grams |
| Dyclonine HCl | 0.6 grams |
| Menthol | 1.0 grams |
| Aspartame | 0.3 grams |
| HPC Klucel LF | 16.1 grams |

The mixture was blended until uniform, at which time the thickened solution was coated to a thickness of 50 mils wet onto a release liner and left in the hood overnight to allow the solvent to evaporate, forming a dried film.

The dried film was pressed using a Carver press under 20,000 p.s.i. at 200° F. for 1-2 min., to 25 mils thickness. This pressed film was then laminated to an adhesive film, 5 mils thick, made as described in Example 1, to form a bilaminate composite. Disks having diameter ½ inch were then die cut from the bilaminate composite.

Disks formed as described above, ½ inch in diameter and 30 mils thick have an active substance-containing layer weighing approximately 100 milligrams. Such a layer (and the disc) therefore contains 5 mg of menthol and 3 mg of Dyclonine HCl.

EXAMPLE X

Comparison of Release of Dyclonine HCl from a Mucoadhesive Disc and from a Sucrets® Lozenge: Disc Affixed to Glass The release profile of Dyclonine HCl into water from a prototype mucoadhesive disc according to the invention and from Sucrets® lozenge were compared as follows.

A Sucrets® lozenge containing 3.0 mg Dyclonine HCl was placed in a Pyrex® flask. A laminated disc made as described in Example 2 above, and containing 3.0 mg Dyclonine HCl, was removed from the release liner and affixed to the inner surface of a second Pyrex® flask by pressing the adhesive surface onto the flask wall. 100 ml deionized water at 25° C. were added to the flasks and the contents of the flasks were stirred priodically.

Thereafter sample aliquots of the aqueous phase were removed from each flask at intervals, and analyzed using UV spectroscopy to determine the amount of Dyclonine HCl released.

Figure 10:
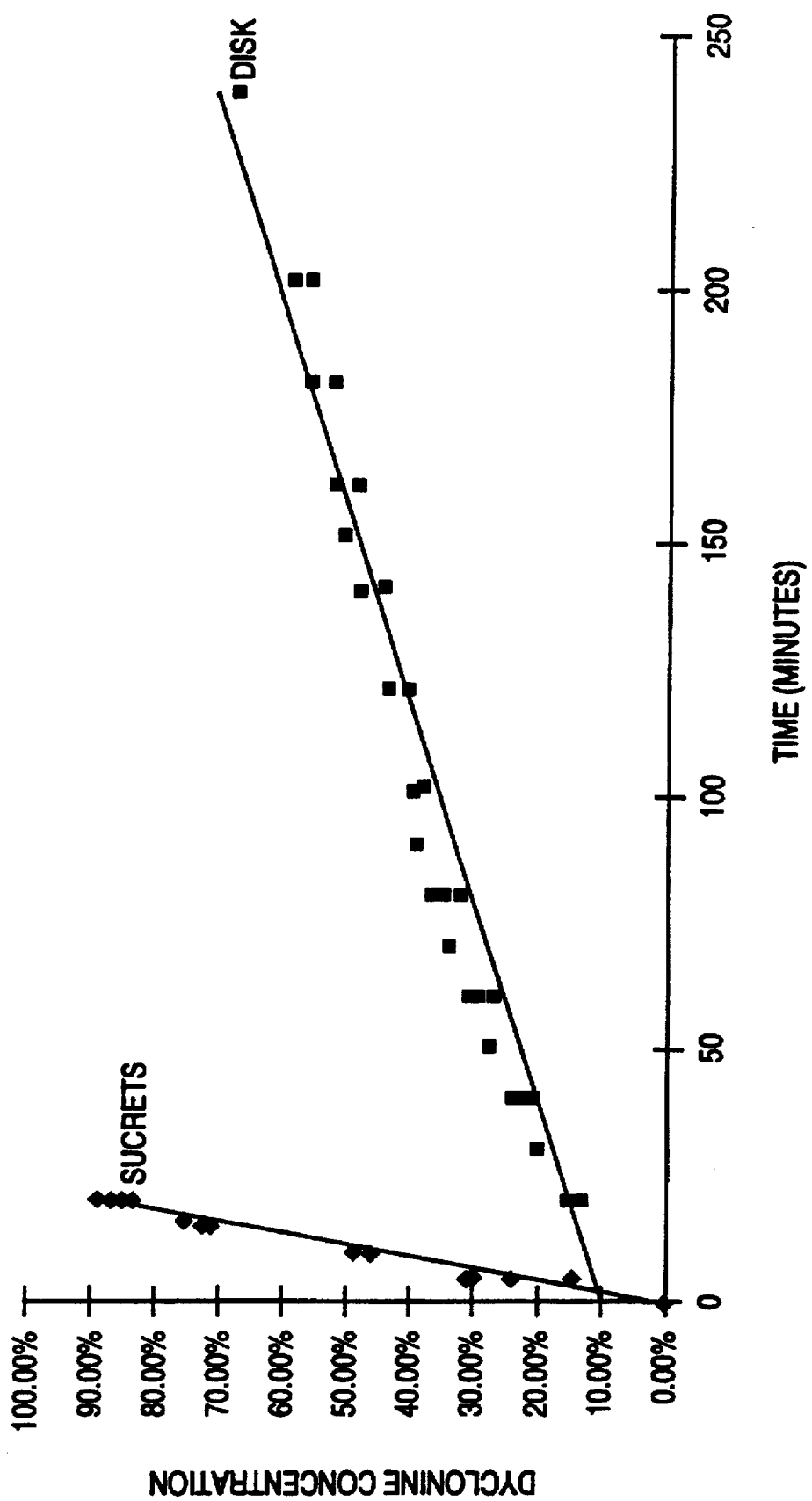
FIG. 10 is a plot of data showing the cumulative release of Dyclonine HCl into water from a mucoadhesive disc according to the invention, and from a Sucrets® lozenge.

The resulting release profiles for both the prototype mucoadhesive disc and the Sucrets lozenge are shown in FIG. 10. FIG. 10 shows the cumulative release of Dyclonine HCl into the water. Although both dosage forms initially contained equivalent amounts of Dyclonine HCl (3.0 mg), the disc gives an appreciably extended and more uniform delivery of the Dyclonine HCl.

EXAMPLE XI

Release of Dyclonine HCl from a Mucoadhesive Disc into a Mucous Surface to Which the Disc is Affixed In this Example, a prototype mucoadhesive disc containing Dyclonine HCl according to the invention was affixed to mucous tissue and the quantity of Dyclonine HCl released into the mucous tissue over an extended time was determined as follows.

A laminated disc was made generally as described in Example IX above, except that it was die cut to ⅜ inch diameter so that it contained 1.11 mg Dyclonine HCl. The disc was removed from the release liner and affixed to a piece of palate tissue (porcine palate) by pressing the adhesive surface of the disc onto a surface of the palate tissue. Then the palate tissue with the disc affixed was immersed in deionized water at 25° C. in a flask the contents of the flask were stirred prior to removing the sample.

After 2 hours, the disc was removed from the palate tissue and the disc was returned to the flask and allowed to dissolve completely (with stirring). Then the amount of Dyclonine HCl in the water was measured. The Dyclonine HCl not accounted for was taken to be an amount that had been delivered to the palate tissue. That is, the difference between the amount of Dyclonine HCl initially present in the disc and the amount that was released into the water is the amount released into the mucous tissue. The results are shown in Table I.

TABLE I

| | |
|---|---|
| Dyclonine HCl initially in the disc | 1.11 mg |
| Dyclonine HCl released to water | 1.04 mg |
| Dyclonine HCl not accounted for | .07 mg |

As Table I shows, after the disc had been affixed to the mucous tissue and suspended in water for 2 hours, only 0.07 mg of Dyclonine HCl (5.8% of the total amount initially contained in the disc) was unaccounted for in the water, and presumably had diffused into the palate tissue.

EXAMPLE XII

Inhibition of Release of Dyclonine HCl from a Trilaminate Mucoadhesive Disc into a Mucous Surface to Which the Disc is Affixed In this Example, a prototype mucoadhesive disc containing Dyclonine HCl according to the invention was constructed with a third layer interposed between the adhesive layer and the active substance-containing layer, for limiting the rate of movement of the active substance into and through the adhesive layer. The trilaminate disc was affixed to mucous tissue and the quantity of Dyclonine HCl released into the mucous tissue over an extended time was determined as described in Example XI.

A laminated disc was made generally as described in Example IX above, except that a thin film (5 mil thickness) of a polymethacrylic copolymer (Eudragit S100) was laminated between the adhesive later and the active substance-containing layer, and the disc was die cut to ⅛ inch diameter so that it contained 1.02 mg Dyclonine HCl. The trilaminate disc was removed from the release liner and affixed to porcine palate tissue, and the release to the palate tissue was determined as described in Example XI. The results are shown in Table II.

TABLE II

| | |
|---|---|
| Dyclonine HCl initially in the disc | 1.02 mg |
| Dyclonine HCl released to water | 0.98 mg |
| Dyclonine HCl not accounted for | .04 mg |

As Table II shows, after the disc had been affixed to the mucous tissue and suspended in water for 2 hours, only 0.04 mg of Dyclonine HCl (3.9% of the total mount initially contained in the disc) was unaccounted for in the water, and presumably had diffused into the palate tissue. The interposition of the limiting layer between the Dyclonine HCl-containing layer and the adhesive layer reduced the amount of Dyclonine HCl diffused into the palate tissue from 5.8% to 3.9%.

EXAMPLE XIII

Comparison of Release of Dyclonine HCl through a Semipermeable Membrane from a Trilaminate Mucoadhesive Disc and from a Bilaminate Mucoadhesive Disc to Which the Disc is Affixed In this Example, bilaminate and trilaminate mucoadhesive discs containing Dyclonine HCl according to the invention were constructed generally as described in examples XI and XII. The discs were affixed to a semipermeable membrane, and the quantity of Dyclonine HCl released through the membrane over an extended time was determined as described in Example 4. Briefly, the disc (½ inch diameter) was placed in a horizontal Franz cell (7.5 ml capacity) separated by a mesh barrier (70 μm Teflon), by affixing an adhesive surface of the disc onto the mesh barrier. Both sides of the cell were filled with nano-filtered water; water in the "donor" side of the cell bathed the surface of the active layer, and water in the "receiver" side of the cell bathed the mesh barrier. The results are shown in Table III.

TABLE III

| | Sample | Dyclonine Release |
|---|---|---|
| Bilaminate disc | 1 | 9.65% |
| Bilaminate disc | 2 | 10.91% |
| Bilaminate disc | 3 | 8.82% |
| | Mean | 9.79 ± 1.05% |
| Trilaminate disc | 1 | 1.45% |
| Trilaminate disc | 2 | 1.43% |
| Trilaminate disc | 3 | 0.30% |
| | Mean, Samples 1 & 2 | 1.44 ± 0.014% |

As Table III shows, the total quantity of Dyclonine passing from the active-containing layer into and through the adhesive layer and then through the semipermeable membrane was greatly reduced by interposition of the occlusive layer between the adhesive layer and the active-containing layer. Particularly, in three experiments for each disc type (bilaminate and trilaminate) shows an average decrease in the release of Dyclonine HCl into the receiver side, from 9.79±1.05% to 1.44±0.014%, after a period of two hours.

EXAMPLE XIV

Figure 11:
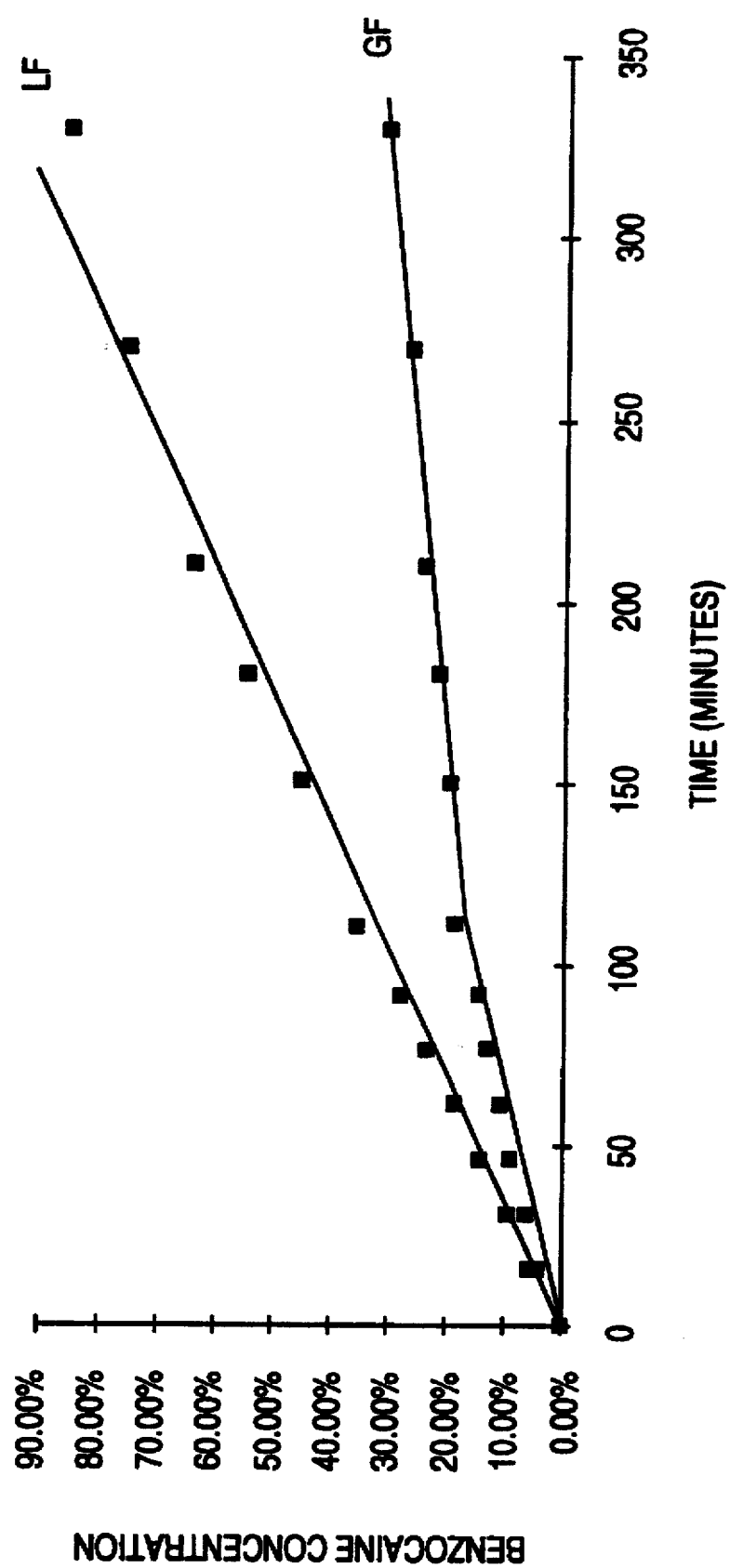
FIG. 11 is a plot of data comparing release of benzocaine into distilled water from mucoadhesive discs according to the invention, having different molecular weight polymers in the active-containing layer.

Release of Benzocaine into Distilled Water from a Mucoadhesive Disc According to the Invention: Effect of Different Molecular Weight of Polymer in the Benzocaine-Containing Layer In this Example, bilaminate mucoadhesive discs containing benzocaine were constructed generally as described in Example IX, substituting benzocaine for Dyclonine. Discs were made using HPC both at the same molecular weight as described in Example 2 (80 k), and at a higher molecular weight (300 k), and the release into distilled water was tested as described in Example X. The results are shown in FIG. 11. These results show a decrease in release rate of benzocaine with increasing molecular weight of HPC in the active-containing layer.

EXAMPLE XV

Transport of Dyclonine HCl and of Benzocaine through Pig Mucosa

In this example, bilaminate mucoadhesive discs, containing as an active substance benzocaine or Dyclonine HCl, were affixed to porcine buccal mucosa and mounted on Franz diffusion cells as described in Example XIII. Avenge amounts of active substance was measured using HPLC, and percents were expressed as a percent of the total initially in the disc.

Particularly, the donor side of the cell was filled with pH 6 buffer and the receiver side was filled with phosphate buffered saline ("PBS"). Samples were taken from the receiver side every thirty minutes for three hours, and the samples were analyzed by HPLC. The average amount and the average percent of active substance appearing in the receiver side after three hours are shown in Table IV.

TABLE IV

| | Average Amount Delivered (μg/cm$^2$) | Average % Transported |
|---|---|---|
| 15% Benzocaine | 284.63 | 3.29 |
| 15% Dyclonine HCl | 282.77 | 3.94 |

The average amount delivered reflects the cumulative amount of drug transported through the mucosa over the three hour period. The average percent delivered represents the cumulative amount of drug transported, in terms of percent of drug contained in the device at the outset. The data show that very low values of benzocaine or Dyclonine HCl were transported through the tissue, and demonstrate that such devices, placed within a mucosa-lined body cavity, such as the oral cavity, can be expected to deliver relatively little of such active substances through the mucosa during the period that the active substance is administered into the body cavity itself.

EXAMPLE XVI

Transport of Dyclonine HCl and of Benzocaine through Human Stratum Corneum

In this example, bilaminate mucoadhesive discs, containing as an active substance benzocaine or Dyclonine HCl, were affixed to human stratum corneum and mounted on Franz diffusion cells. The donor side of the cell was filled with pH 6 buffer and the receiver side was filled with PBS. Samples were taken from the receiver side and analyzed using HPLC, and the average amount and percentage of active substance appearing in the receiver cell were determined. The average amount and the average percent of active substance appearing in the receiver side are shown in Table V.

For both benzocaine and Dyclonine HCl the amount of active substance delivered through the human stratum corneum (Example XVI) is lower than the amount of active substance delivered through the pig buccal mucosa (Example XV). For administration of Dyclonine HCl or benzocaine into the oral cavity of a human subject, so that the active substance is carried by the saliva to the irritated tissues of the mouth and throat, it is desirable to limit the amount of active substance delivered through the oral mucosal surface to which the device is affixed. Preferably a device for delivery of active substances for relief of cough and sore throat is affixed to the palate. The transfer coefficient for human palate tissue is lower than that for pig buccal mucosa and higher than that for human stratum corneum, and Examples XV and XVI thus provide an approximate range within which the extent to which delivery of active substances across the underlying human palate mucosa can be expected to fall. For a device according to the invention, affixed to the palate, the great majority of benzocaine or Dyclonine HCl can be expected to be delivered into the oral cavity.

TABLE V

|  | Average Amount Delivered (µg/cm²) | Average % Transported |
|---|---|---|
| 15% Benzocaine | 255.56 | 2.42 |
| 15% Dyclonine HCl | 14.60 | 0.18 |

Interposition of a third layer, relatively impermeable to the active agent, between the active agent-containing layer and the adhesive layer, as described for example in Example XII, can reduce further the quantity of active agent passing through the mucosa. As the results in Examples XV and XVI show, however, a bilaminate system can be suitable for delivery.

Long-Lasting Mucoadhesive Device for Administration of Breath-Freshening Agent

Generally, the breath freshening device according to the invention is constructed as a laminated composite including a basal adhesive layer constructed of a water soluble pressure sensitive mucoadhesive composition; and an odorant containing layer constructed of a water soluble polymer mixed with the odorant. Optionally the device may include a third layer, interposed between the adhesive layer and the odorant containing layer, constructed of a water soluble polymer that is substantially impermeable or is poorly permeable to the constituents of the odorant.

The device may be made by forming the respective layers as films and then laminating the films, and finally cutting (as, for example, by die cutting) the device from the laminate.

The films may be made from polymer mixtures by any of a variety of techniques known in the polymer film-forming art, including casting, calendaring, coating, and extrusion. Batch processing techniques may be employed, but for large scale production, continuous processing can be preferred. Die extrusion through a slit is a particularly suitable continuous processing technique for making the films for use in the devices according to the invention.

Lamination may be carried out by contacting the films and applying pressure. Laminated films may be made in small quantities by use of a press, but for continuous pressing the films can be pressed together using one or more rollers. Heat may be applied to the films as they are brought together, for example by heating the press or by heating the roller or rollers.

Referring again now to FIG. 8, a bilaminate device configuration according to the invention suitable for a breath freshening device is shown generally at 50. The device includes a basal adhesive layer 56 constructed of a water soluble pressure sensitive mucoadhesive composition, and an upper odorant containing layer 52 constructed of a water soluble polymer mixed with the odorant 54.

A trilaminate device configuration suitable for a breath freshening device is shown generally at 60 in FIG. 9. The trilaminate device includes a basal adhesive layer 56 constructed of a water soluble pressure sensitive mucoadhesive composition, and an upper odorant containing layer 52 constructed of a water soluble polymer mixed with the odorant 54, generally as in the bilaminate device shown in FIG. 8. The trilaminate device additionally includes a third layer 62, interposed between layer 52 and layer 56, constructed of a water soluble polymer that is substantially impermeable or poorly permeable to the constituents of the odorant.

The devices as shown in the Figs. are provided with a release liner 58, which is peeled away from the device just prior to use.

The content of the layers is described in greater detail below.

1. The adhesive layer.

Suitable GRAS certified polymers for use in the water soluble pressure sensitive mucoadhesives include poly(vinyl pyrrolidone) ("PVP"), poly(vinyl alcohol) ("PVA"), hydroxy propyl cellulose ("HPC"), poly(ethylene oxide) ("PEO"), poly(acrylic acid) ("PAA"), polyacrylates such as Carbopol 934, starch and starch derivatives, polysaccharides, sodium carboxymethyl cellulose ("Na-CMC"), xanthan gum, karaya gum, and gelatin, among others. Suitable plasticizers include, for example and particularly for oral-mucosal contact and other use in the oral cavity, glycerin, sorbitol, any of the glycols, polysorbate 80, triethyl titrate, acetyl triethyl titrate, and tributyl citrate.

In particular embodiments the water soluble pressure sensitive mucoadhesive includes as a polymer PVP (about 30–60 weight %), HPC (about 10–30 weight %); and glycerin as a plasticizer (about 10–60 weight %). In these formulations, the molecular weight of the PVP is in the range about 30,000–1,000,000; and the molecular weight of the HPC is in the range about 60,000–1,000,000. Such compositions adhere quickly on contact and without moistening to oral mucosal surfaces and to oral cavity prostheses or other devices of the poly(methyl methacrylate) ("PMMA") type, and continue to adhere well to such surfaces for extended times in the milieu of the oral cavity.

The water soluble pressure sensitive adhesive layer may take the form of a film which preferably is about 5–10 mils thick.

Preferably the adhesive layer additionally includes a preservative, such as for example BHA or BHT, in a suitable small quantity. The adhesive additionally may include a certified colorant.

2. The odorant-containing layer.

Suitable GRAS certified polymers for use in the odorant containing layer include, particularly, hydroxypropyl cellulose ("HPC").

The term "odorant", as used herein, refers to a substance or combination of substances which, when present in the fluids of a subject's oral cavity, impart a pleasing smell to the person's exhalant breath. A breath freshening substance may work in part by addition of a desirable odor to the breath, and in part as a "reodorant", that is, by masking an unpleasant odor in the subject's breath, and the term "odorant" herein includes such reodorant effects.

As is well recognized in the flavorist's art, the appreciation of flavor is a complex response, principally, to the senses of aroma and taste. See generally, e.g., G. Reiniccius, ed. (1994), *Source Book of Flavors*, 2d Ed., Chapman & Hall (herein, the "*Source Book of Flavors*"). The various tastes (sweet, salt, sour, bitter) are due to nonvolatile components of the flavor, while the aroma or odor is due to volatile components. The chemical makeup of a flavor, and particularly of the volatile components of a flavor, may be exceedingly complex, with a number of volatile components contributing significantly to the distinctive aroma. On the other hand, certain chemical compounds are by themselves when smelled reminiscent of a particular flavor, even where the flavor that is recalled is in fact complex. Such character impact compounds include, for example, Menthol (having the character impact of peppermint); L-Carvone (spearmint); Methyl salicylate (wintergreen); and Citral (lemon).

A straightforward way to provide desired odorant in the odorant-containing layer of a breath freshening device according to the invention is to add to the polymer of the layer an essential oil (i.e., a volatile oil) of a plant material. The *Source Book of Flavors* describes essential oils that are in common use in the flavoring industry, including descriptions of methods for their industrial production and an account of their chemistry.

Any of a variety of breath freshening odorants may be delivered to the oral cavity by adding into the polymer of the odorant-containing layer a flavoring that includes the odorant. In at least some cultures, mint-like odorants are acceptable and even desireable on the breath, and accordingly the odorant containing layer of a suitable breath freshening device can include a mint flavoring, as described more fully below.

Preferably the odorant coning layer additionally includes a preservative, such as for example BHA or BHT in a suitable small quantity. Optionally the odorant containing layer additionally includes a sweetener, most preferably a non-sugar sweetener, such as aspartame in a suitable small quantity.

3. Mint odorants.

Mint odorants can be provided by essential oils derived by extraction and distillation from leaves and/or flowering parts of any of various plants. The composition of such distillates depends, among other things, upon the species and variety of plant, as well as its geographical origin, and upon the method of extraction and degree of distillation. A variety of mint flavorings are described, for example in the *Source Book of Flavors*. They include, particularly for example, oil of peppermint, the chief aromatic constituents of which are menthol, merithone, and menthyl acetate; oil of spearmint, the chief aromatic constituent of which is L-Carvone; and oil of wintergreen, the chief aromatic constituent of which is Methyl salicylate.

4. Device fabrication.

As pointed out generally above, the layers can be produced using techniques known in the art of polymer film fabrication, by conventional batch process or by continuous process, as for example by conventional die extrusion through a slit. Typically, for example, batch processing can be carried out as follows. The components making up each layer (e.g., the adhesive layer, or the odorant containing layer, or an intermediate layer) are blended together either with a suitable solvent to aid in mixing or, as may be more preferable, without a solvent. The blending may be carded out at an elevated temperature (particularly where no solvent is employed), to aid in homogeneous mixing of the components. The blended components of each layer are thereafter pressed m a film having the desired final layer thickness using a heated Carver press. The resulting films are then laminated, for example by contacting them and applying pressure. Generally, for example, a conventional continuous die extrusion process entails feeding the components of the layer to an extruder, such as a twin screw extruder. The extruder melt blends the components of the layer and then forces the blended mixture continuously through a slit whose thickness is selected to provide the desired thickness in the resulting film. The individual films may be robed for temporary storage before lamination, or the lamination may be carried out immediately following extrusion. The films are continuously laminated by bringing the films into contact and pressing them together over a roller or between rollers, which may as appropriate be heated to facilitate the lamination process.

Individual devices are then cut from the completed laminate, for example by punching or die cutting, and stored for use.

The examples that follow are presented by way of illustration only, and are not meant as limiting the invention.

EXAMPLE XVII

Construction of Device for Delivery of Peppermint

This example illustrates the construction of a device for delivery of a refined (reduced) oil of peppermint. The oil of peppermint used in this example is a "Reduced Oil of Peppermint FCC/NF "Rose Mitcham" ", which is commercially available from the A. M. Todd Company of Kalamazoo, Mich. It contains the following mint flavor components:

| | |
|---|---|
| menthofuran (GLC) | 02.6% |
| menthol | 57.0 |
| menthone | 24.8 |
| menthyl acetate | 07.4 |

As provided from the commercial source, this reduced oil of peppermint has a specific gravity 0.903, an optical rotation −28.2, and a refractive index 1.4600. It is soluble in three volumes of 70% ethanol.

1. Construction of the odorant coning layer.

In this example, the odorant containing layer is constructed by thoroughly mixing the peppermint oil (as described above), a non-sugar sweetener (Aspartame), and a preservative (BHA) with a hydroxypropyl cellulose ("HPC") polymer, and then extruding the odorant containing polymer mixture through a slit to form a film. Preferably a twin screw extruder is employed, and the components are continuously fed into the extruder, in which the blending is effected. In this particular example, the odorant containing layer has these ingredients in the following proportions.

| Klucel HPC GF | 83.5% |
|---|---|
| Peppermint oil | 15.0 |
| Aspartame | 1.50 |
| BHA | 0.0083 |

2. Construction of the adhesive layer.

In this example, the adhesive layer is constructed by thoroughly mixing an HPC polymer with a poly vinylpyrrolidone ("PVP") polymer, with glycerol as a plasticizer, with a food colorant, and with a preservative (BHA), and then extruding the adhesive polymer mixture through a slit to form a film. In this particular example, the adhesive layer has these ingredients in the following proportions.

| PVP (K90) | 47.0% |
|---|---|
| Glycerin | 37.0 |
| Klucel HPC GF | 16.0 |
| FD & C #40 | 0.024 |
| BHA | 0.0020 |

The formed adhesive film and odorant containing film are then laminated by passing the films together between rollers under pressure, and the individual devices are die cut from the resulting laminated composite.

EXAMPLE XVIII

Tack and Adhesion Properties of the Adhesive Layer

The properties of tack and adhesion of the water soluble pressure sensitive mucoadhesive employed in the breath freshening device of the invention were tested as follows.

An adhesive film was made generally as described in Example XVII.

Tack and work of adhesion were measured using a Texture Technologies TXA.XT2 Texture Analyzer in which a PMMA probe was used in place of the usual SS probe. A 5 mil thick adhesive film made as described in Example XVII was tested under the following conditions.

| Probe speed (penetration): | 1.0 mm/sec |
|---|---|
| Penetration depth: | 0.10 mm |
| Dwell time: | 10 sec |
| Probe speed (withdrawal): | 5.0 mm/sec |
| Probe diameter: | 0.80 cm |

All measurements were made at room temperature (20°–25° C.).

The resulting trace of the force during withdrawal versus time allowed for a determination for each sample of both the tack (the peak maximum, in Kg) as well as the work of adhesion (area under the peak curve, in Kg-sec). Films were tested dry as well as after moistening by spraying the dry film surface with a fine mist of distilled water, followed by a resting time of 60 seconds to allow for hydration of the sample.

In this example, the above test protocol was applied to films according to the invention (indicated as "BFD" in the Figs.), and to constructed with the following compositions.

"279-190": 60% PEO 301; 30% HPC MF; 5% PE; 3% PG; 2% PEG 400 (described in Schiraldi U.S. Pat. No. 4,731,243).

"279-191": 55.3% NaPAA; 37.5% HPC HF; 6.3% Glycerin (described in Chang U.S. Pat. No. 4,373,036).

"310-30B#2": 40% RPC HF; 35.5% PVP 90 F; 20% RPC LF; 2% Mentha Oil; 2% Menthol; 0.5% Fennel Oil (described in Hisahige JP 63-209797).

"310-44" 44.5% PVP 90 F; 30% HPC LF; 10% RPC RF; 10% PEG 400; 2.5% Menthol; 2.0% Mentha Oil; 1.0% Fennel Oil (described in Hisahige JP 63-209797).

Figure 14:
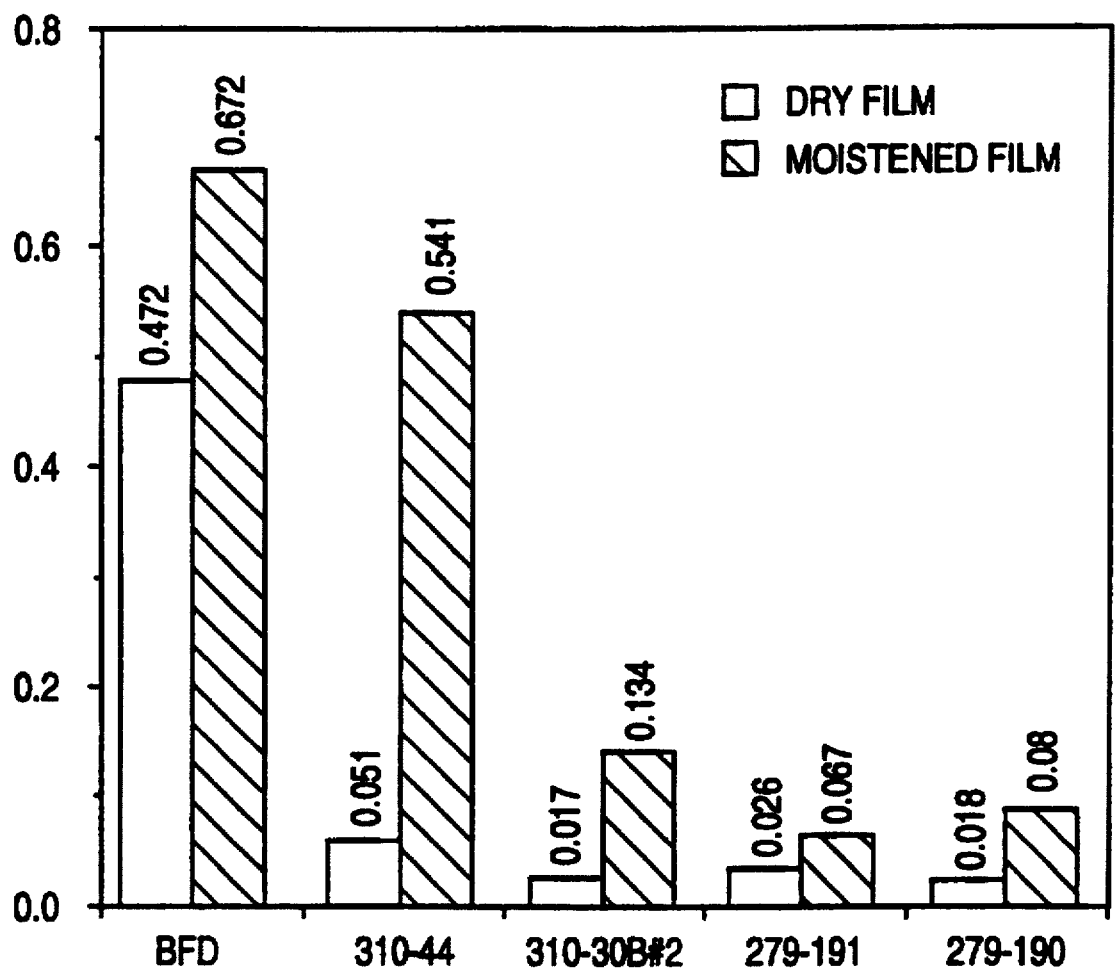
FIG. 14 is a graph comparing tack characteristics, on a PMMA surface, of dry and of moistened adhesive films according to the invention with tack characteristics of conventional films.
Figure 15:
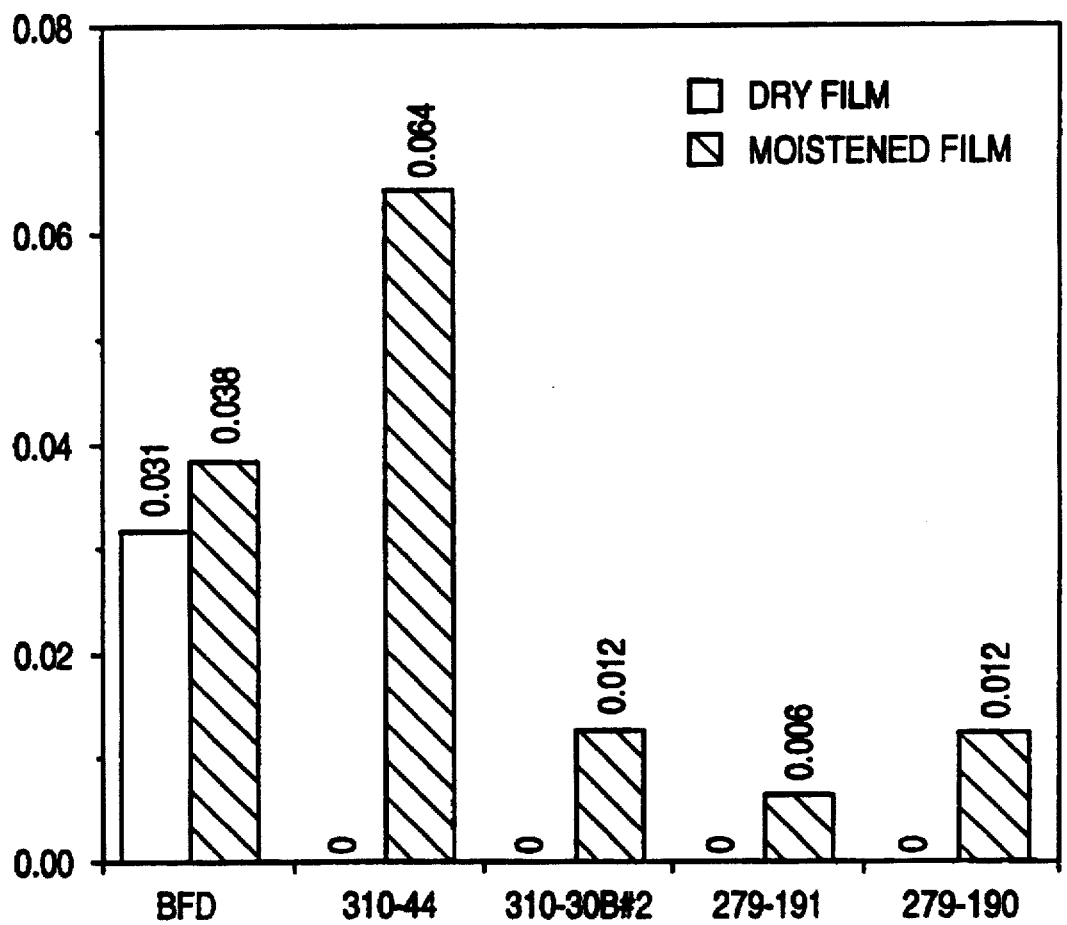
FIG. 15 is a graph comparing adhesion characteristics, on a PMMA surface, of dry and of moistened adhesive films according to the invention with adhesion characteristics of conventional films.

The results are shown in FIGS. 14 and 15. In these tests the adhesive film according to the invention is significantly more adhesive toward the PMMA probe in the dry state (i.e., before moistening) than did four other formulations tested. Following moistening the adhesive film according to the invention was comparably adhesive or was more adhesive toward the PMMA probe than were the other tested formulations.

EXAMPLE XIX

Flexibility of Odorant Containing Layer

As noted above, water soluble polymers such a hydroxypropyl cellulose that dissolve suitably slowly in the milieu of the oral cavity may not themselves be sufficiently flexible for use in an odorant containing layer in a device according to the invention. Conventionally, the layer would be rendered more flexible by addition of a suitable plasticizer such as glycerol. We have discovered that the essential oils of Spearmint, or Peppermint, and of Wintergreen can provide substantial and sufficient plasticizing effect when mixed with HPC in quantities suitable for extended delivery of mint odorant to the oral cavity at breath freshening rates.

In this example, the elastic moduli (as a measure of flexibility) are compared for film preparations of HPC containing no additional components, and of film preparations containing 15 weight % of oil of peppermint, oil of spearmint, oil of wintergreen, and oil of lemon. This conventional measurement entails measuring the tensile force per unit cross sectional area (stress) of a sample of the film during elongation of the sample at a fixed rate (strain). The elastic modulus is derived from the stress/strain curve. In this example, the test was carried out on bone-shaped film samples 5 mils thick and 0.25 inch wide, gage length 1.0 inch, at an elongation rate of 0.2 inch/min. All samples were tested at room temperature (20°–25° C.).

Figure 16:
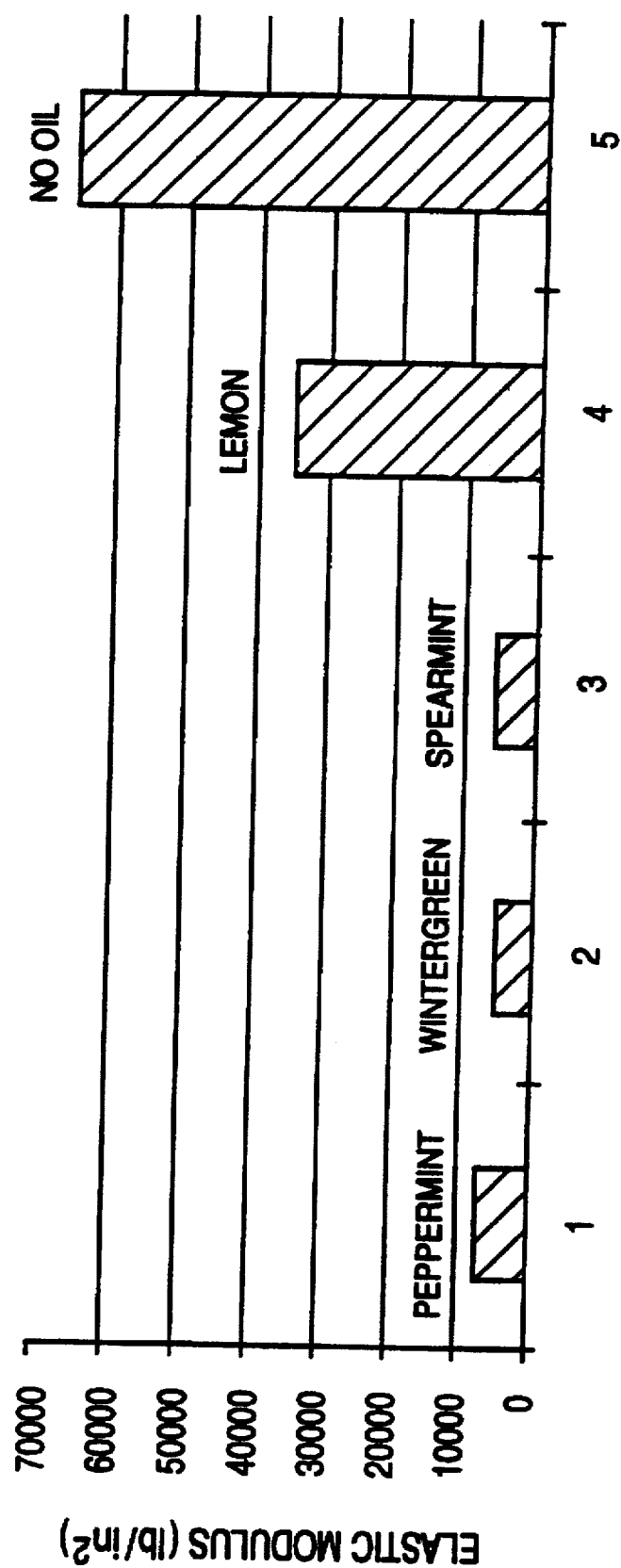
FIG. 16 is a graph comparing elastic moduli of HPC films, illustrating the plasticizing effect of mint odorants.

The results are shown in FIG. 16. As the Fig. shows, addition of any of the mint odorants to the HPC composition results in a substantially and sufficiently flexible film, while addition of lemon oil does not sufficiently lower the elastic modulus of the film. Thus, where a mint odorant is used, no additional plasticizer is required in the odorant containing layer.

EXAMPLE XX

Delivery of Peppermint over Extended Times

In this example, the capacity for delivering a breath-freshening substance into an aqueous medium was compared in devices according to the invention and in a "breath mint" that is commercially marketed under the name "Certs®". A flavor containing film was constructed, generally as described in Example XVII. Portions of the film ½ inch in diameter and 25 mils thick, each containing 8.6 mg menthol were immersed in distilled water, and breath mint tablets each containing 4.3 mg menthol were immersed in distilled water in separate flasks, and the flasks were continuously shaken. Samples were withdrawn from the flasks after elapsed times of 15 min., 30 min., 45 min., 60 min., and 120 min., and the quantity of menthol was analyzed by gas chromatography.

Figure 17:
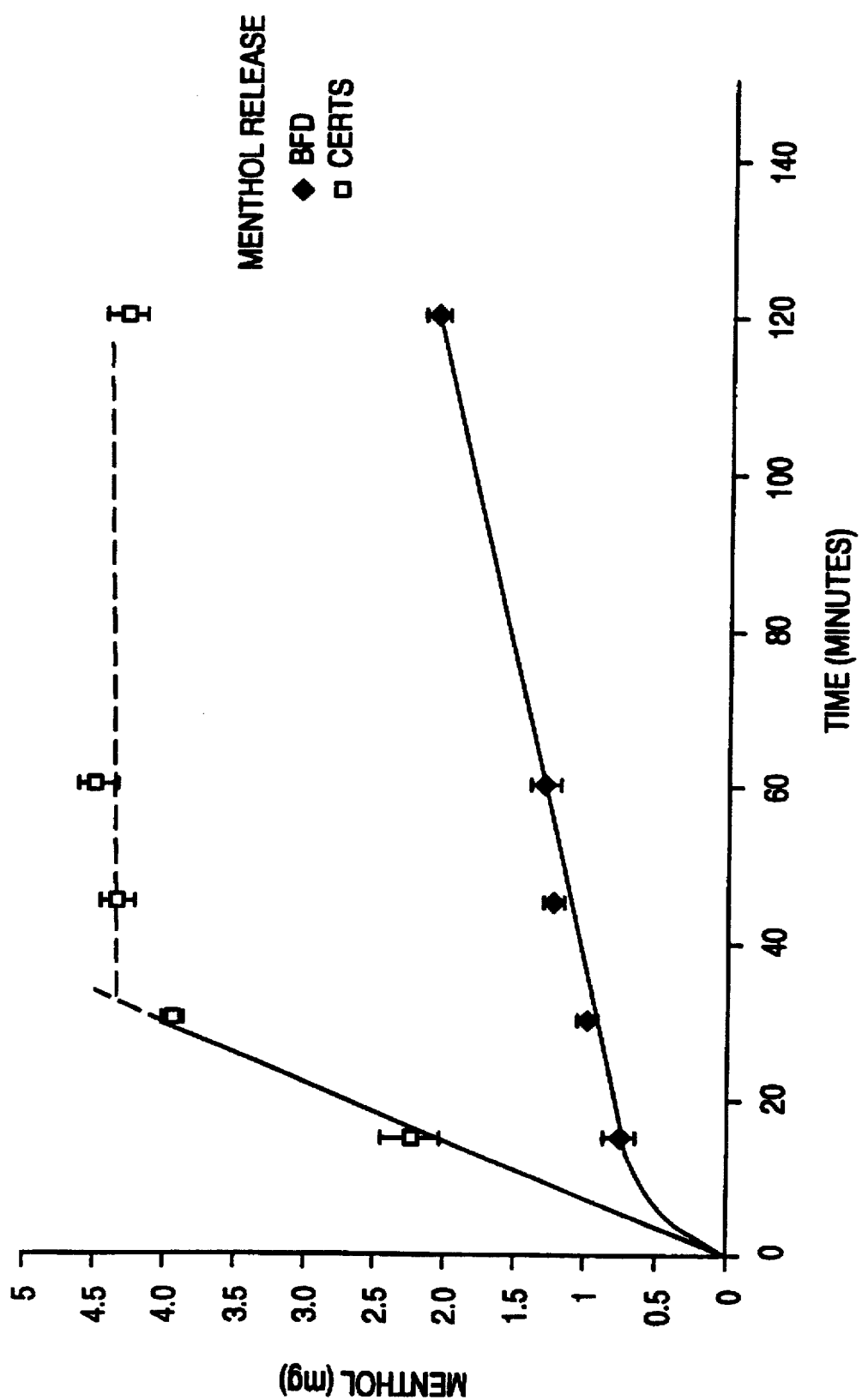
FIG. 17 is a graph comparing menthol release over time from a breath freshening device according to the invention and from a conventional commercially marketed "breath mint"(Certs®).

The results are shown in FIG. 17. On average, the breath freshening device of the invention had by the first (fifteen minute) sample interval released about 0.7 mg menthol, and thereafter the device delivered menthol at a continuous steady rate throughout the sampling period; at the two hour sampling interval, approximately 2.0 mg of the original 8.6 mg of menthol had been released from the device, and rate of delivery was continuing at slightly less than 0.25 mg per hour. By contrast, each breath mint had on average by the first sampling interval released nearly half its total quantity of menthol, and had nearly exhausted their delivery capacity at the second (thirty minute) sampling interval.

In a person's mouth, the saliva is swallowed more or less continuously, and once a conventional breath mint has been completely dissolved, the breath freshening effect wanes quickly as the residual odorant is flushed away. As the example shows, the invention can provide for a sustained and steady supply of the breath freshening odorant to the saliva flow, resulting in an extended breath freshening effect.

EXAMPLE XXI

Evaluation of Breath-Freshening Effect

In this example, the breath freshening effectiveness of devices according to the invention, constructed generally as described in Example XVII above, were informally evaluated by volunteers. The volunteers reported that the device was convenient to use, was non-obtrusive, did not materially interfere with speech, and left a pleasant taste and odor in the mouth.

Other Embodiments

Other embodiments are within the following claims.

For example, the water-soluble pressure-sensitive adhesives according to the invention can be used to affix transdermal devices to human skin. Because the materials in the adhesive are GRAS certified, they can result in an adhesive product having very low skin irritation and reaction.

The water-soluble pressure-sensitive adhesives of the invention can act as a reservoir for diffusional delivery of a substance into the mucosa-lined body cavity (such as the oral cavity or gastrointestinal tract, or the vaginal cavity), or for delivery of a substance transmucosally through the area of adhesive contact. Preferably for such applications, the adhesive is provided in film form, and is loaded with a suitable quantity of the substance to be delivered. For use in transmucosal delivery, one surface of the adhesive film makes adhesive contact with the mucosal surface; preferably the other surface of the adhesive film is covered with a substance-occlusive backing layer made of a material that is poorly soluble in water or in the fluid secretions of the body cavity in which the film is used. Examples of substance-occlusive poorly soluble materials that are safe for oral use include poly(dimethyl siloxane), poly(tetrafluoro ethylene), cellulose acetate, and copolymers of neutral methacrylic acid esters with one or both of methacrylic acid and diethylaminoethyl methacrylate.

In a dental prosthesis adhesive film application, for example, the adhesive can be loaded with a flavoring or a mouth deodorant to act as a breath freshener, or with an antibacterial. Suitable flavorings, mouth deodorants, and antibacterials are known in the oral hygiene art. As the adhesive slowly dissolves, the agent is gradually released into the oral cavity.

Or, in a dental prosthesis adhesive film application, the adhesive can be loaded with a substance to be delivered transmucosally; in this configuration, the dental prosthesis works as an occlusive backing.

The water-soluble pressure-sensitive adhesives of the invention can be employed as an adhesive layer in a laminated device for diffusional delivery of an agent within a mucosa-lined body cavity. Such laminated devices can take any of a variety of forms, and may have just one layer in addition to the adhesive (such as the substance-occlusive poorly soluble layer described above, for example), or many additional layers.

Water-soluble pressure-sensitive adhesive films according to the invention can be made by other processes than described above. Where a press is used to form the film, for example, different temperatures may be used, according to the particular polymer composition.

Alternatively, the molten polymer may be extruded through a slit die to form a film of the desired thickness; or it can be extruded or cast as a single film between release surfaces. In the latter case, the product can be cut to a shape appropriate to the particular application, and the release liners can be peeled away just prior to use.

Other embodiments are within the following claims, and variations on the embodiments shown by way of example above have been made and can be altered as may be desired. For example, with reference to Examples 1 and 2, aspartame can be left out and a flavor imparting a different taste or odor can be added instead. Also, the loading of actives dydonine HCl, menthol, and cineole can be controlled by either varying the concentration or changing the thickness of the disc. Other active substances useful for relief of sore throat pain or cough can be delivered according to the invention.

We claim:

1. A water-soluble pressure-sensitive adhesive comprising a water-soluble polymer and a water-soluble plasticizer, said polymer having a T(g) or a T(m) greater than about 25° C. and having a hydrophilicity greater than about 25%, said plasticizer being miscible with said polymer at room temperature and being liquid at room temperature and having a boiling point higher than 80° C.

2. The water-soluble pressure sensitive adhesive of claim 1 wherein said polymer has a T(g) or a T(m) greater than about 30° C.

3. The water-soluble pressure-sensitive adhesive of claim 1, said polymer comprising poly(vinyl pyrrolidone) and said plasticizer comprising glycerol.

4. The water-soluble pressure-sensitive adhesive of claim 3, said polymer further comprising hydroxy propyl cellulose.

5. The water-soluble pressure-sensitive adhesive of claim 3, comprising 95–40 weight % poly(vinyl pyrrolidone), 0–50 weight % hydroxy propyl cellulose, and 11–60 weight % glycerol.

6. The water-soluble pressure-sensitive adhesive of claim 5, said glycerol being present in the range 30–50 weight %.

7. The water-soluble pressure-sensitive adhesive of claim 1, in film form.

8. A dental prosthesis adhesive, comprising the water-soluble pressure-sensitive adhesive film of claim 7, shaped to conform to a portion of the mucosal surface-contacting surface of the dental prosthesis.

9. A laminated device for the controlled release of a substance within a mucosa-lined body cavity, said device comprising:

the water-soluble adhesive layer comprised of the water-soluble adhesive of claim 1; and a water-soluble polymer layer;
wherein the substance is dissolved or dispersed in either or both of said adhesive or polymer layers.

10. The device of claim 9 wherein the device provides delayed-onset delivery of the substance.

11. The device of claim 10 wherein the polymer layer is substantially impermeable to the substance and does not contain the substance.

12. The laminated device of claim 11, said polymer layer being insoluble in water that is below 40° C.

13. The laminated device of claim 12, said polymer layer comprising hydroxypropyl cellulose and sorbitan monostearate.

14. The device of claim 13 wherein the substance is a breath reodorant.

15. The device of claim 9 comprising one or more polymer layers and two or more substances to be delivered.

16. The device of claim 15 wherein the substances are delivered sequentially.

17. A laminated device for the controlled release of a substance within a mucosa-lined body cavity, said device comprising:
 a water-soluble adhesive layer comprised of the water-soluble pressure-sensitive adhesive of claim 1;
 a first water-soluble polymer layer; and
 a second water-soluble polymer layer;
wherein the substance is dissolved or dispersed in any or all of said adhesive or polymer layers.

18. The device of claim 17 wherein the adhesive layer and the second polymer layer contain the substance and wherein the first polymer layer is disposed between the adhesive layer and the second polymer layer, and wherein the device provides for pulsatile delivery of the substance.

19. The device of claim 18 wherein the pulsatile delivery includes periods of no delivery of the substance.

20. The device of claim 17 further comprising a third polymer layer wherein the first and the third polymer layers contain the substance and wherein the first polymer layer is disposed between the adhesive layer and the second polymer layer and the second polymer layer is disposed between the first polymer layer and the third polymer layer and wherein the device provides for pulsatile delivery of the substance.

21. The device of claim 20 wherein the pulsatile delivery includes periods of no delivery of the substance.

22. A laminated device for the controlled release of a substance within a mucosa-lined body cavity comprising the substance dissolved or dispersed in a water-soluble pressure-sensitive adhesive layer comprising the water-soluble adhesive of claim 1.

23. A laminated composite device for delivering a substance into the oral cavity for relief of sore throat or cough, comprising a water soluble polymer film layer containing the active ingredient, and the water soluble pressure sensitive mucoadhesive layer of claim 1.

24. The laminated composite of claim 23 wherein the active ingredient is a medicament for the relief of sore throat pain.

25. The laminated composite of claim 24 wherein the active ingredient is selected from the group consisting of benzocaine, lidocaine and dyclonine.

26. The laminated composite of claim 23 wherein the active ingredient is a medicament for the relief of cough.

27. The laminated composite of claim 26 wherein the active ingredient is selected from the group consisting of dextromethorphan HBR, nospine, codeine phosphate, menthol.

28. The laminated composite of claim 24 additionally comprising a medicament for the relief of cough.

29. The laminated composite of claim 23 wherein the active-containing water soluble layer comprises a hydrophobic material that will not dissolve in water below 40° C. and is hot water dispersible.

30. The laminated composite of claim 29 wherein the active-containing water soluble layer is selected from the group of materials consisting of monoglycerides, triglycerides, waxes, fatty acids, fatty alcohols and mixtures thereof.

31. The laminated composite of claim 23 wherein the polymer is selected from the group consisting of poly(vinyl pyrrolidone), poly(vinyl alcohol), hydroxy propyl cellulose, poly(ethylene oxide), poly(acrylic acid), polyacrylates, starch and starch derivatives, polysaccharides, sodium carboxymethyl cellulose, xanthan gum, karaya gum, and gelatin or mixtures thereof.

32. The laminated composite of claim 23 wherein the plasticizer is selected from the group consisting of glycerin, sorbitol, glycol, polysorbate 80, triethyl citrate, acetyl triethyl citrate and tributyl citrate.

33. The laminated composite of claim 23 further including a third polymer layer interposed between the adhesive layer and the active-containing layer.

34. A method for administering a substance over an extended time period for relief of sore throat or cough, comprising dissolving or dispersing the substance in a laminated water soluble device having the water soluble pressure sensitive adhesive layer of claim 1, and affixing the device onto a mucosal surface of the oral cavity.

35. The method of claim 34 wherein the substance is a medicament for the relief of sore throat pain.

36. The method of claim 35 wherein the medicament is selected from the group consisting of benzocaine, lidocaine and dyclonine.

37. The method of claim 34 wherein the substance is a medicament for the relief of cough.

38. The method of claim 37 wherein the medicament is selected from the group consisting of dextromethorphan HBR, noscpine, codeine phosphate.

39. The method of claim 38 additionally comprising a medicament for the relief of cough.

40. A method for administering a substance over an extended time period for relief of sore throat or cough, comprising dissolving or dispersing the substance in a laminated water soluble device having the water soluble pressure sensitive adhesive layer of claim 1, and affixing the device onto a mucosal surface of the oral cavity.

41. The device of claim 40, being a device for delivery of a substance to the subject.

42. The delivery device of claim 41, said device being constructed to deliver a substance into the body cavity in which the device is emplaced.

43. The delivery device of claim 41, said device being constructed to deliver a substance across a mucosal surface to which the basal pressure-sensitive adhesive surface of the device is affixed.

44. The device of claim 40, being a laminated device structure, wherein the water-soluble pressure sensitive portion comprises a basal layer of the device.

45. A laminated device for administering a mint aroma into the oral cavity over an extended time, said device including a basal layer comprising the water soluble pressure sensitive mucoadhesive polymer composition of claim 1, and an upper layer comprising a water soluble polymer composition and a mint flavoring.

* * * * *

UNITED STATES PATENT AND TRADEMARK OFFICE
CERTIFICATE OF CORRECTION

PATENT NO. : 5,700,478
DATED : December 23, 1997
INVENTOR(S) : James E. Biegajski, et. al.

It is certified that error appears in the above-indentified patent and that said Letters Patent is hereby corrected as shown below:

Figure 14, top horizonal axis should be identified as "TACK (Kg)"

Figure 15, top horizonal axis should be identified as "WORK OF ADHESION (Kg-sec)"

Column 2, line 39, "a" should be --an--

Column 3, line 6, "note" should be --noted--

Column 4, line 43, after "least" insert --)--
        line 53, "adehere" should be --adhere--

Column 7, line 16, delete "."
        line 34, each occurrence, "titrate" should be --citrate--
        line 35, "titrate" should be --citrate--

Column 13, line 4, "One" should be --one--

Column 18, line 4, "Hydochloride" should be --Hydrochloride--
        line 22, after Kollidon" insert --®--
        line 67, "CLEF" should be --(EF--

Column 20, line 67, "." should be --,--

UNITED STATES PATENT AND TRADEMARK OFFICE
CERTIFICATE OF CORRECTION

Page 2 of 3

PATENT NO. : 5,700,478
DATED : December 23, 1997
INVENTOR(S) : James E. Biegajski, et. al.

It is certified that error appears in the above-indentified patent and that said Letters Patent is hereby corrected as shown below:

Column 22, line 12, "polvinyl" should be --polyvinyl--

Column 24, line 2, "priodically" should be --periodically--
        line 33, "flask the" should be --flask. The--
Column 25, line 24, "mount" should be --amount--

Column 26, line 31, "Avenge" should be --Average--

Column 28, line 50, each occurrence, "titrate" should be --citrate--

Column 29, line 66, "merithone" should be --menthone--

Column 30, line 18, "m" should be --to--
        line 21, "Generally" should begin new paragraph
        line 26, "robed" should be --rolled--
        line 60, "coning" should be --containing--

Column 32, line 3, each occurrence, "RPC" should be --HPC--
        line 6, "RPC" should be --HPC--
        line 22, "a" should be --as--

Column 35, line 64, "nospine" should be --noscpine--

UNITED STATES PATENT AND TRADEMARK OFFICE
CERTIFICATE OF CORRECTION

PATENT NO. : 5,700,478
DATED : December 23, 1997
INVENTOR(S) : James E. Biegajski, et. al.

It is certified that error appears in the above-indentified patent and that said Letters Patent is hereby corrected as shown below:

Column 36, line 21, "23" should be --32--
line 62, "the" should be --a--

Signed and Sealed this

Fourth Day of August, 1998

Attest:

BRUCE LEHMAN

Attesting Officer

Commissioner of Patents and Trademarks